(12) United States Patent
Hill et al.

(10) Patent No.: US 9,458,179 B2
(45) Date of Patent: Oct. 4, 2016

(54) QUINUCLIDINE, 1-AZABICYCLO[2.2.1]HEPTANE, 1-AZABICYCLO[3.2.1]OCTANE, AND 1-AZABICYCLO[3.2.2]NONANE COMPOUNDS AS ALPHA-7 NICOTINIC ACETYLCHOLINE RECEPTOR LIGANDS

(71) Applicant: BRISTOL-MYERS SQUIBB COMPANY, Princeton, NJ (US)

(72) Inventors: Matthew D. Hill, Wallingford, CT (US); Haiquan Fang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/400,948

(22) PCT Filed: May 20, 2013

(86) PCT No.: PCT/US2013/041783
§ 371 (c)(1),
(2) Date: Nov. 13, 2014

(87) PCT Pub. No.: WO2013/177024
PCT Pub. Date: Nov. 28, 2013

(65) Prior Publication Data
US 2015/0322089 A1 Nov. 12, 2015

Related U.S. Application Data

(60) Provisional application No. 61/651,093, filed on May 24, 2012.

(51) Int. Cl.
| | | |
|---|---|---|
| C07D 519/00 | (2006.01) | |
| C07D 471/20 | (2006.01) | |
| C07D 453/02 | (2006.01) | |
| C07D 498/20 | (2006.01) | |

(52) U.S. Cl.
CPC ........... *C07D 519/00* (2013.01); *C07D 453/02* (2013.01); *C07D 471/20* (2013.01); *C07D 498/20* (2013.01)

(58) Field of Classification Search
CPC  C07D 453/02; C07D 471/20; C07D 498/20; C07D 519/00
USPC ............... 546/18; 544/182, 183, 230, 94; 514/278, 228.1
See application file for complete search history.

(56) References Cited

U.S. PATENT DOCUMENTS

| | | |
|---|---|---|
| 5,053,412 A | 10/1991 | Fisher et al. |
| 7,863,291 B2 | 1/2011 | Cook, II et al. |
| 8,278,320 B2 | 10/2012 | McDonald et al. |
| 8,309,577 B2 | 11/2012 | Cook, II et al. |
| 8,481,555 B2 | 7/2013 | Lentz et al. |
| 8,507,516 B2 | 8/2013 | McDonald et al. |

FOREIGN PATENT DOCUMENTS

EP    0 452 101 B1    7/1999

OTHER PUBLICATIONS

Gündisch, D. et al., "Nicotinic acetylcholine receptor ligands, a patent review (2006-2011)", Expert Opin. Ther. Patents, vol. 21, No. 12, pp. 1867-1896 (2011).

*Primary Examiner* — Rita Desai
(74) *Attorney, Agent, or Firm* — James Epperson

(57) ABSTRACT

The disclosure provides compounds of formula I, including their salts, as well as compositions and methods of using the compounds. The compounds are ligands for the nicotinic α7 receptor and may be useful for the treatment of various disorders of the central nervous system, especially affective and neurodegenerative disorders.

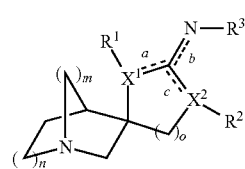

7 Claims, No Drawings

QUINUCLIDINE, 1-AZABICYCLO[2.2.1]HEPTANE, 1-AZABICYCLO[3.2.1]OCTANE, AND 1-AZABICYCLO[3.2.2]NONANE COMPOUNDS AS ALPHA-7 NICOTINIC ACETYLCHOLINE RECEPTOR LIGANDS

BACKGROUND OF THE INVENTION

The disclosure generally relates to compounds of formula I, including their salts, as well as compositions and methods of using the compounds. The compounds are ligands, agonists and partial agonists for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood, however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs pre-synaptically. The localization of α7 nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the α7 receptor, such as α7 agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The α7 agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks. This clinical data is consistent with pre-clinical data showing α7 agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause disregulation of signaling through α7 nicotinic receptors. Deletion of the α7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ42 and α7 receptors. Treatment with α7 agonists and partial agonists may represent an approach for disease modification in Alzheimer's disease. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., JPET Fast Forward, Sep. 28, 2009, DOI: 10.1124/jpet.109.154633), an α7 agonist was shown to decrease weight gain and food intake and reduce the elevated plasma levels of triglycerides, glucose, glycated hemoglobin and TNFa in a mouse model of type II diabetes (db/db mice which are deficit in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacol. (2007) 151:915-929; Romanelli, et al, ChemMedChem (2007) 2 (6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacol. and Therapeutics (2009), doi:10:1016/j.pharmthera.2009.03.009).

Ligands for the nicotinic α7 receptor have been disclosed in the references above, and also in U.S. Pat. No. 7,863,291, and US patent application publications US20110269787, US20110263605, and US20100099684.

The invention provides technical advantages, for example, the compounds are novel and are ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds formula I, including pharmaceutically acceptable salts, and compositions and methods of treatment using these compounds. The compounds may be useful for the treatment of various disorders of the central nervous system:

One aspect of the invention is a compound of formula I, or a stereoisomer thereof,

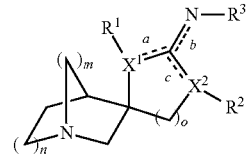

wherein
$X^1$ is nitrogen; $X^2$ is nitrogen; m is 1 or 2; n is 1 or 2; o is 1 or 2; a is a single bond; b is a single bond; c is a double bond; $R^1$ is selected from the group consisting of hydrogen, methyl, and ethyl; $R^2$ is absent;

or $X^1$ is nitrogen; $X^2$ is oxygen; m is 1 or 2; n is 1 or 2; o is 1 or 2; a is a double bond; b is a single bond; c is a single bond; $R^1$ is absent; $R^2$ is absent;

or $X^1$ is oxygen; $X^2$ is nitrogen; m is 1 or 2; n is 1 or 2; o is 1 or 2; a is a single bond; b is a single bond; c is a double bond; $R^1$ is absent; $R^2$ is absent;

or $X^1$ is oxygen; $X^2$ is nitrogen; m is 1 or 2; n is 1 or 2; o is 1; a is a single bond; b is a double bond; c is a single bond; $R^1$ is absent; $R^2$ is methyl;

$R^3$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinazolinyl, quinoxalinyl, naphthyridinyl, indazolyl, indolyl, 2-indolonyl, benzisoxazolyl, benzoisothiazolyl, benzoxazolyl, benzothiazolyl, benzimidazolyl, furopyridinyl, oxazolopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, imidazopyridinyl, pyrrolopyrimidinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5 (6H)-onyl, and tetrahydrobenzothiazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^4R^5$, pyrrolidinonyl, methylenedioxy, furyl, thienyl, pyrazolyl, imidazolyl, thiazolyl, triazolyl, pyrazinyl, pyrimidinyl, naphthyl, $C_{1-4}$alkylamido, $CONR^4R^5$, pyridyl, phenyl, and benzyl, and where imidazolyl, pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^4R^5$;

R⁴ is hydrogen, C₁₋₄alkyl, C₁₋₄hydroxyalkyl, or C₁₋₄aminoalkyl; and
R⁵ is hydrogen, C₁₋₄alkyl, C₁₋₄hydroxyalkyl, or C₁₋₄aminoalkyl;
or R⁴ and R⁵ taken together with the nitrogen atom to which they are attached is azetidinyl, pyrrolidinyl, piperidinyl, piperazinyl, N—(C₁₋₄alkyl)piperazinyl, morpholinyl, or homopiperidinyl;
or a pharmaceutically acceptable salt thereof.

Another aspect of the invention is a compound of formula I or Ia where
X¹ is nitrogen; X² is nitrogen; m is 2; n is 1; o is 1; a is a single bond; b is a single bond; c is a double bond; R¹ is selected from the group consisting of hydrogen, methyl, and ethyl; R² is absent;
or X¹ is nitrogen; X² is oxygen; m is 2; n is 1; o is 1; a is a double bond; b is a single bond; c is a single bond; R¹ is absent; R² is absent;
or is oxygen; X² is nitrogen; m is 2; n is 1; o is 2; a is a single bond; b is a single bond; c is a double bond; R¹ is absent; R² is absent;
or X¹ is oxygen; X² is nitrogen; m is 2; n is 1; o is 1; a is a single bond; b is a double bond; c is a single bond; R¹ is absent; R² is methyl;
R³ is selected from the group consisting of thiazolyl, pyridinyl, pyrazinyl, pyridazinyl, pyrimidinyl, triazinyl, quinolinyl, isoquinolinyl, quinazolinyl, quinoxalinyl, indazolyl, benzoxazolyl, benzothiazolyl, benzimidazolyl, oxazolopyridinyl, thiazolopyridinyl, thiazolopyridinonyl, thiazolopyrazinyl, thiazolopyrimidinyl, triazolopyridinyl, imidazopyridinyl, and pyrrolotriazinyl, and is substituted with 0-3 substituents independently selected from the group consisting of C₁₋₄alkyl, C₁₋₄haloalkyl, C₁₋₄alkoxy, benzyloxy, halo, NR⁴R⁵, imidazolyl, and phenyl;
R⁴ is C₁₋₄alkyl; and
R⁵ is C₁₋₄alkyl;
or a pharmaceutically acceptable salt thereof.

Another aspect of the invention is a compound of formula I or Ia where X¹ is nitrogen; X² is nitrogen; m is 2; n is 1; o is 1; a is a single bond; b is a single bond; c is a double bond; R¹ is selected from the group consisting of hydrogen, methyl, and ethyl; R² is absent; or a pharmaceutically acceptable salt thereof.

Another aspect of the invention is a compound of formula I or Ia where X¹ is nitrogen; X² is oxygen; m is 2; n is 1; o is 1; a is a double bond; b is a single bond; c is a single bond; R¹ is absent; R² is absent; or a pharmaceutically acceptable salt thereof.

Another aspect of the invention is a compound of formula I or Ia where X¹ is oxygen; X² is nitrogen; m is 2; n is 1; o is 2; a is a single bond; b is a single bond; c is a double bond; R¹ is absent; R² is absent; or a pharmaceutically acceptable salt thereof.

Another aspect of the invention is a compound of formula I or Ia where X¹ is oxygen; X² is nitrogen; m is 2; n is 1; o is 1; a is a single bond; b is a double bond; c is a single bond; R¹ is absent; R² is methyl; or a pharmaceutically acceptable salt thereof.

Another aspect of the invention is a compound of formula I or Ia where R³ is selected from the group consisting of thiazolyl, pyridinyl, pyrazinyl, pyridazinyl, pyrimidinyl, triazinyl, quinolinyl, isoquinolinyl, quinazolinyl, quinoxalinyl, indazolyl, benzoxazolyl, benzothiazolyl, benzimidazolyl, oxazolopyridinyl, thiazolopyridinyl, thiazolopyridinonyl, thiazolopyrazinyl, thiazolopyrimidinyl, triazolopyridinyl, imidazopyridinyl, and pyrrolotriazinyl, and is substituted with 0-3 substituents independently selected from the group consisting of C₁₋₄alkyl, C₁₋₄haloalkyl, C₁₋₄ alkoxy, benzyloxy, halo, NR⁴R⁵, imidazolyl, and phenyl; R⁴ is C₁₋₄alkyl; and R⁵ is C₁₋₄alkyl; or a pharmaceutically acceptable salt thereof.

Another aspect of the invention is a compound of formula I or Ia where R³ is selected from the group consisting of thiazolyl, (phenyl)thiazolyl, pyridinyl, (halo)pyridinyl, pyrazinyl, (halo)pyrazinyl, (halo)pyrazinyl, pyridazinyl(halo)pyridazinyl, pyrimidinyl, (alkoxy)pyrimidinyl, (halo)pyrimidinyl, (imidazolyl)pyrimidinyl, triazinyl, (alkyl)triazinyl, (dialkyl)triazinyl, quinolinyl, isoquinolinyl, quinazolinyl, quinoxalinyl, indazolyl, (haloalkyl)indazolyl, benzoxazolyl, (alkyl)benzoxazolyl, (halo)benzoxazolyl, benzothiazolyl, (alkoxy)benzothiazolyl, (alkyl)benzothiazolyl, (halo)benzothiazolyl, benzimidazolyl, oxazolopyridinyl(alkyl)oxazolopyridinyl, thiazolopyridinyl, (alkoxy)thiazolopyridinyl, (benzyloxy)thiazolopyridinyl, (halo)thiazolopyridinyl, (dialkylamino)thiazolopyridinyl, thiazolopyridinonyl, thiazolopyrazinyl, (alkyl)thiazolopyrazinyl, (alkoxy)thiazolopyrazinyl, (halo)thiazolopyrazinyl, thiazolopyrimidinyl(alkoxy)thiazolopyrimidinyl, triazolopyridinyl, imidazopyridinyl, pyrrolotriazinyl, (alkyl)pyrrolotriazinyl, and (halo)pyrrolotriazinyl; or a pharmaceutically acceptable salt thereof.

Another aspect of the invention is a compound of formula I according to Formula Ia;

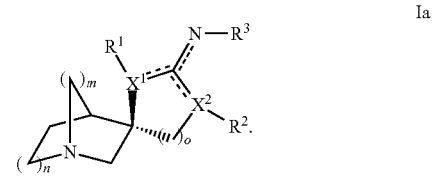

Another aspect of the invention is a compound of formula I or Ia where R³ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, (pyrrolidinylCO)thiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, methoxypyridinylpyridazinyl, pyrimidinyl, (bromo)(isopropyl)pyrimidinyl, (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, and phenylpyrazinyl, and dimethyltriazinyl; or a pharmaceutically acceptable salt thereof.

Another aspect of the invention is a compound of formula I or Ia where $R^3$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, (pyrrolidinylCO)benzothiazolyl, methylsulfonylbenzothiazolyl, chlorothiazolopyridinyl, dimethylthiazolopyridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, chlorotriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy) thiazolopyrimidinyl, quinolinyl, bromoquinolinyl, fluoroquinolinyl, methylquinolinyl, (methyl)(methoxy)quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, and 7,8-dihydroquinazolin-5 (6H)-onyl; or a pharmaceutically acceptable salt thereof.

Another aspect of the invention is a compound of formula I or Ia where $R^3$ is selected from the group consisting of phenylthiazolyl, (chloro)(methyl)pyridinyl, (bromo)(phenyl)pyrimidinyl, methoxypyrimidinyl, difluoromethoxypyrimidinyl, difluoroethoxypyrimidinyl, cyclopentoxypyrimidinyl, (methyl)(methoxy)pyrimidinyl, (methoxyphenyl) pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinoinyl, and quinazolinyl or a pharmaceutically acceptable salt thereof.

Another aspect of the invention is a compound or formula I or Ia where $R^3$ is selected from the group consisting of thiazolyl, pyridinyl, pyridazinyl, pyrimidinyl, pyrazinyl, benzothiazolyl, thiazolopyridinyl, indazolyl, benzimidazolyl, isoquinoinyl, and quinazolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^4R^5$, pyrrolidinonyl, methylenedioxy, furyl, thienyl, triazolyl, pyrimidinyl, naphthyl, $C_{1-4}$alkylamido, $CONR^4R^5$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^4R^5$; or a pharmaceutically acceptable salt thereof.

Another aspect of the invention is a compound or formula I or Ia where $R^3$ is selected from the group consisting of pyridinyl, pyrimidinyl, pyrazinyl, thiazolopyridinyl, and isoquinoinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^4R^5$, pyrrolidinonyl, methylenedioxy, furyl, thienyl, triazolyl, pyrimidinyl, naphthyl, $C_{1-4}$alkylamido, $CONR^4R^5$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^4R^5$; or a pharmaceutically acceptable salt thereof.

Another aspect of the invention is a compound or formula I or Ia where $R^3$ is selected from the group consisting of pyridinyl and isoquinoinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^4R^5$, pyrrolidinonyl, methylenedioxy, furyl, thienyl, triazolyl, pyrimidinyl, naphthyl, $C_{1-4}$alkylamido, $CONR^4R^5$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^4R^5$; or a pharmaceutically acceptable salt thereof.

Another aspect of the invention is a compound of formula I where $R^3$ is selected from the group consisting of thiazole, thiadiazole, isoxazole, oxazole, pyrazole, imidazole, pyridine, pyrazine, pyridazine, pyrimidine, quinoline, isoquinoline, quinoxaline, indazole, indole, 2-indolone, benzothiazole, benzimidazole, benzoxazole, benzo(d)isothiazole, benzisoxazole, isothiazolo-[5,4-b]pyridine, (1,2,4)-triazolo [1,5-a]pyridine, thiazolo[5,4-b]pyridine and tetrahydrobenzothiazole in which each group is optionally substituted with one or two substituents selected from the group consisting of $C_{1-4}$alkyl, $C_{1-4}$alkoxy, halogen, hydroxy, cyano, trifluoromethyl, difluoromethyl, fluoromethyl, trifluoromethoxy, difluoromethoxy, $C_{1-4}$alkylsulfonyl, furyl, morpholino, methylenedioxy, pyridyl, $C_{1-4}$alkylphenyl, halophenyl, dimethylaminophenyl, $C_{1-4}$alkylamido, —$CONR^4R^5$ in which $R^4$ and $R^5$ each are independently hydrogen, $C_{1-4}$alkyl, hydroxy $C_{1-4}$alkyl, amino $C_{1-4}$alkyl or $R^4$ and $R^5$ taken together with the atom to which they are attached are $C_{3-6}$ cycloalkyl; phenyl, substituted phenyl, phenylmethyl, substituted phenylmethyl in which said substituted phenyl and substituted phenylmethyl are substituted with substituents independently selected from the group consisting of halogen, $C_{1-4}$alkyl, $C_{1-4}$alkoxy, trifluoromethyl and trifluoromethoxy; or a pharmaceutically acceptable salt thereof.

For a compound of formula I or Ia, the scope of any instance of a variable substituent, including $X^1$, $X^2$, $R^1$, $R^2$, and $R^3$, a, b, c, m, n, and o can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$ (CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

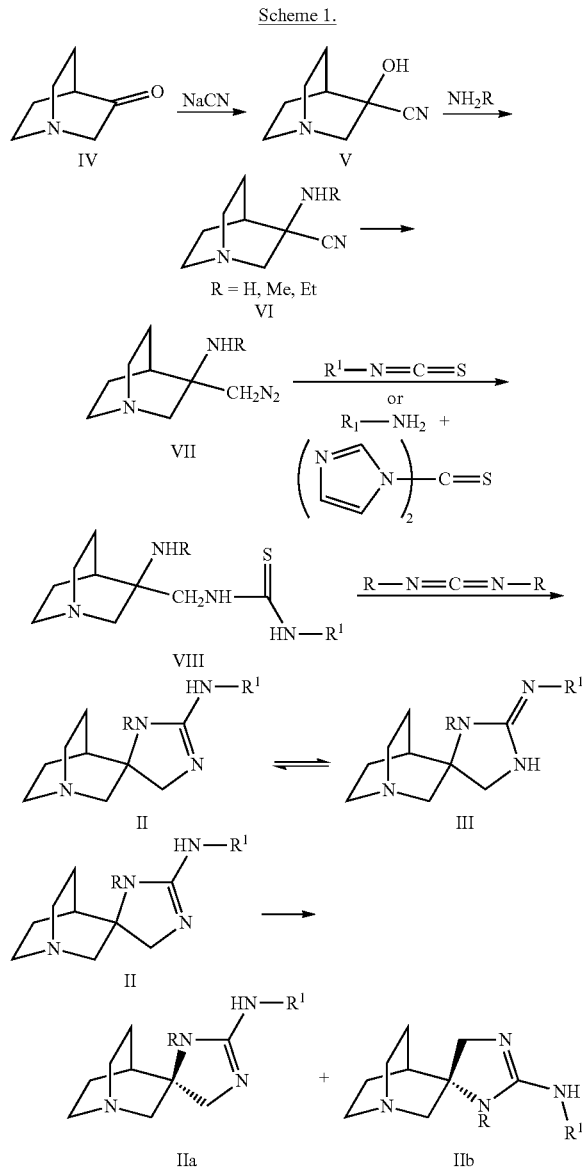

Compounds of Formula II can be prepared as illustrated in Reaction Scheme 1. The ketone of Formula IV (3-quinuclidone) is known, is commercially available, or may be prepared by methods known to those skilled in the art. The ketone can be converted to the corresponding cyanohydrin of Formula V by reaction with sodium or potassium cyanide plus an acid. The compound of Formula V can be converted to the corresponding amino compound of Formula VI by reaction with the corresponding amine. The compound of Formula VI can be reduced to the corresponding diamine VII using lithium aluminum hydride.

The compound of Formula VII can be reacted with heteroaryl isothiocyanates directly in an inert solvent to give the thioureas of Formula VIII. Alternatively, the heteroarylamine can be reacted with thiocarbonyl-diimidazole to give an activated species which can be used without isolation to convert the compound of Formula VII to the compound of Formula VIII. The heteroarylamine may be prepared by methods known to those skilled in the art.

The thiourea of Formula VIII can be cyclized using, for example, di-isopropyl carbodiimide to give the imidazoline-containing final product of Formula II and its tautomer, Formula III, as a racemate. The compound of Formula I may be resolved into pure enantiomer compounds of Formula IIa and Formula IIb by means known in the art, for example, via chiral chromatography.

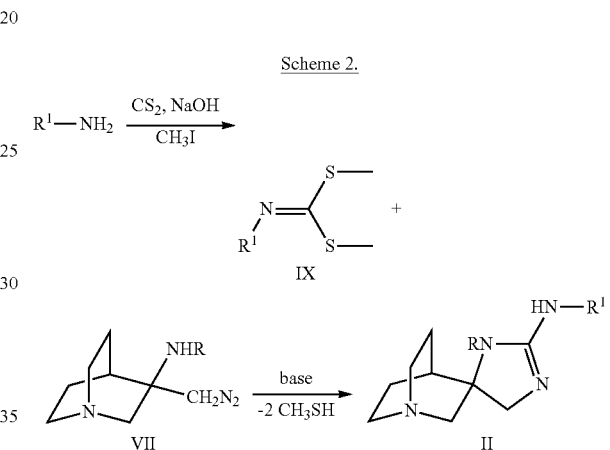

Additionally, the (hetero)aromatic amines may be reacted with carbon disulfide, sodium hydroxide, and methyl iodide to give intermediate dimethyl carbonimidodithioates IX (reaction Scheme 2). These can be reacted with diamine VII in the presence of base to eliminate two moles of methanethiol and generate desired products II directly.

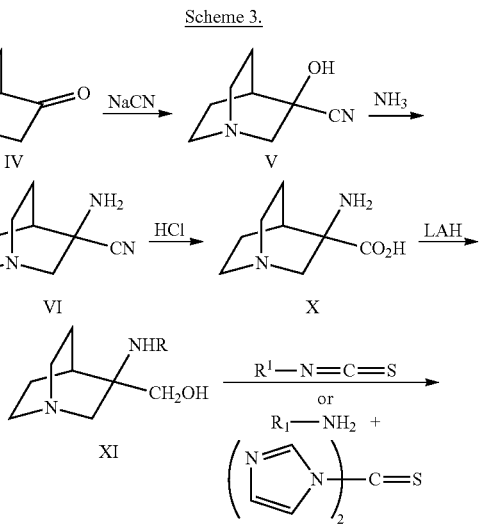

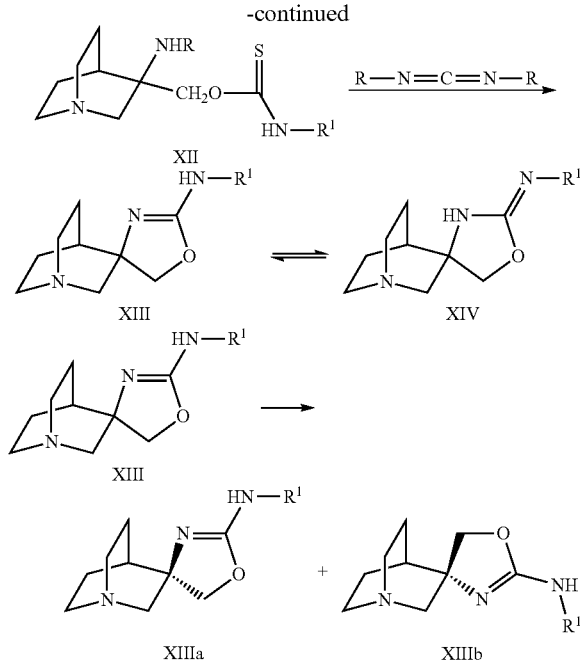

Compounds of Formula XIII are prepared as illustrated in Reaction Scheme 3. The aminonitrile VI (prepared as described above) can be converted to the carboxylic acid of formula X by treatment with HCl (aq). The compound of Formula X can be reduced to the corresponding aminoalcohol of Formula XI by reaction with lithium aluminum hydride.

The compound of Formula XI can be reacted with heteroaryl isothiocyanates directly in an inert solvent to give the thioureas of Formula XII. Alternatively, the heteroarylamine can be reacted with thiocarbonyl-diimidazole to give an activated species which can be used without isolation to convert the compound of Formula XI to the compound of Formula XII. The heteroarylamine may be prepared by methods known to those skilled in the art.

The thiourea of Formula XII can be cyclized using, for example, di-isopropyl carbodiimide to give the imidazoline-containing final product of Formula XIII and its tautomer, Formula XIV, as a racemate. The compound of Formula XIII may be resolved into pure enantiomer compounds of Formula XIIIa and Formula XIIIb by means known in the art, for example, via chiral chromatography.

Scheme 4.

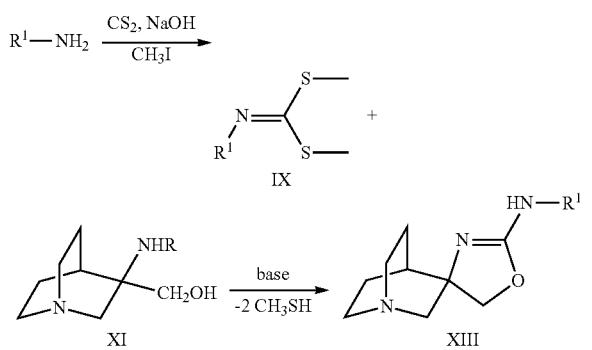

Additionally, the (hetero)aromatic amines may be reacted with carbon disulfide, sodium hydroxide, and methyl iodide to give intermediate dimethyl carbonimidodithioates IX (reaction Scheme 4). These can be reacted with aminoalcohol XI in the presence of base to eliminate two moles of methanethiol and generate desired products XIII directly.

Scheme 5.

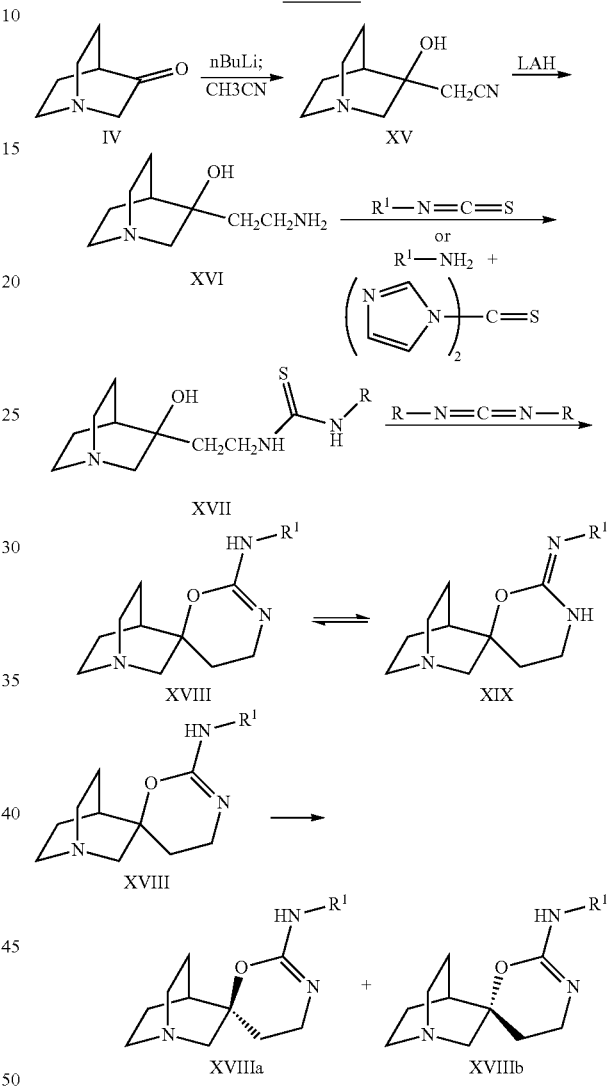

Compounds of Formula XVIII can be prepared as illustrated in Reaction Scheme 5. Ketone IV can be converted to the nitrile of formula XV by treatment with n-butyl lithium, followed by acetonitrile addition. The compound of Formula XV can be reduced to the corresponding aminoalcohol of Formula XVI by reaction with lithium aluminum hydride.

The compound of Formula XVI can be reacted with heteroaryl isothiocyanates directly in an inert solvent to give the thioureas of Formula XVII. Alternatively, the heteroarylamine can be reacted with thiocarbonyl-diimidazole to give an activated species which can be used without isolation to convert the compound of Formula XVI to the compound of Formula XVII. The heteroarylamine may be prepared by methods known to those skilled in the art.

The thiourea of Formula XVII can be cyclized using, for example, di-isopropyl carbodiimide to give the imidazoline-containing final product of Formula XVIII and its tautomer, Formula XIX, as a racemate. The compound of Formula XVIII may be resolved into pure enantiomer compounds of Formula XVIIIa and Formula XVIIIb by means known in the art, for example, via chiral chromatography.

Scheme 6.

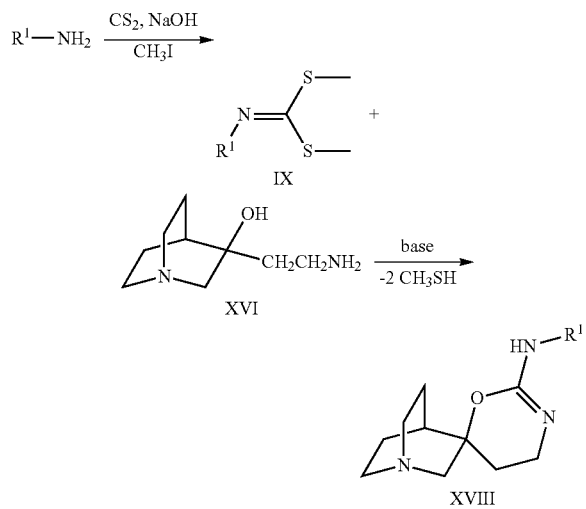

Additionally, the (hetero)aromatic amines may be reacted with carbon disulfide, sodium hydroxide, and methyl iodide to give intermediate dimethyl carbonimidodithioates IX (reaction Scheme 6). These are reacted with aminoalcohol XVI in the presence of base to eliminate two moles of methanethiol and generate desired products XVIII directly.

Scheme 7.

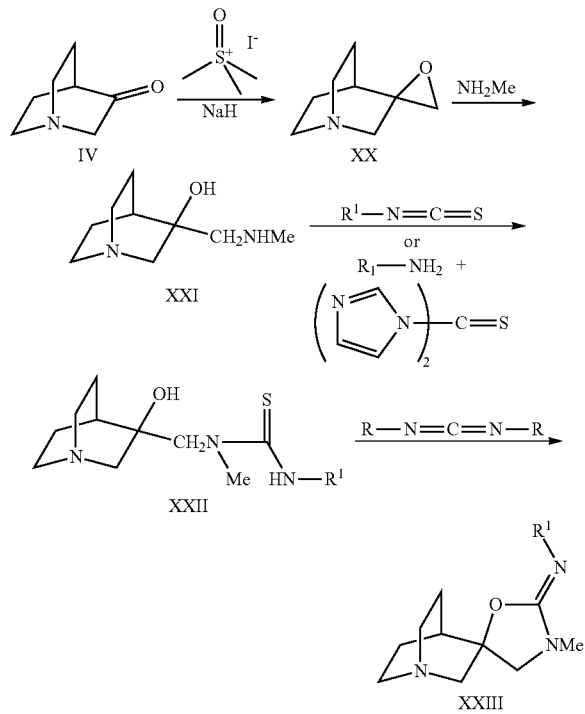

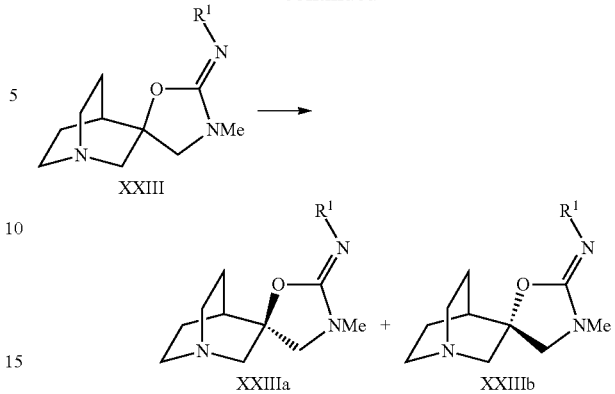

Compounds of Formula XXIII can be prepared as illustrated in Reaction Scheme 7. Ketone IV can be converted to the epoxide of formula XX by treatment with sodium hydride and trimethylsulfoxonium iodide. The compound of Formula XX can be opened to the corresponding aminoalcohol of Formula XXI by reaction with methylamine.

The compound of Formula XXI can be reacted with heteroaryl isothiocyanates directly in an inert solvent to give the thioureas of Formula XXII. Alternatively, the heteroarylamine can be reacted with thiocarbonyl-diimidazole to give an activated species which can be used without isolation to convert the compound of Formula XXI to the compound of Formula XXII. The heteroarylamine may be prepared by methods known to those skilled in the art.

The thiourea of Formula XXII can be cyclized using, for example, di-isopropyl carbodiimide to give the imidazoline-containing final product of Formula XXIII as a racemate. The compound of Formula XXIII may be resolved into pure enantiomer compounds of Formula XXIIIa and Formula XXIIIb by means known in the art, for example, via chiral chromatography.

Biological Methods

I) α7 Nicotinic Acetylcholine Receptor Binding.

Membranes were prepared for binding using HEK293 cells stably expressing the rat α7 nicotinic acetylcholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α-7 for Nicotinic Acetylcholine Receptor Channel Function in Mammalian Cells ("FLIPR").

Summary:

Lead compounds are evaluated for agonist activity at α-7, α3β4, α4αβ2, and α1β1δ1ε sub-types of nicotinic ACh receptor ion channels expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., *Nature Reviews*, 2003, 4:579-586; Gonzalez J. E., et al., *Receptors and Channels*, 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods:

Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo. G418 and Minimal Essential Medium were purchased from InVitrogen Life Technologies, Carlsbad, Calif. Fetal bovine serum was purchased from (InVitrogen, Carlsbad, Calif.).

Cell Culture:

HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ Flux Assays of $Ca^{2+}$ Channels Expressed in HEK-293 Cells:

HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis:

The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos Quantification Assay:

Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminiscence detection kit (catalog #89860, EZ-detect c-Fos Trans kit, Pierce Biotechnology Inc., Rockford, Ill.).

IV) MK-801 Disrupted Set-Shift Assay in Rats:

This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of specific compounds described herein and tested in the above assay (II) is provided in Tables 1-4.

TABLE 1

| Example Number | R | $R_1$ | FLIPR α7-HI ($EC_{50}$, nM) | FLIPR α7-HI ($EC_{50}$, nM) |
|---|---|---|---|---|
| 1 | H | benzothiazole-2-yl with 6-OMe | | ++ |
| 2 | Me | benzothiazole-2-yl with 6-OMe | | ++ |

TABLE 1-continued

Structure: bicyclic core with HN—R¹ substituent, RN and N ring atoms (as shown).

| Example Number | R | R₁ | FLIPR α7-HI (EC₅₀, nM) | FLIPR α7-HI (EC₅₀, nM) |
|---|---|---|---|---|
| 3 | Et | 2-(6-methoxy-benzothiazolyl) | | ++ |
| 4 | H | 5-phenyl-thiazol-2-yl | 2,958 | + |
| 5 | Me | 5-phenyl-thiazol-2-yl | | + |
| 6 | Et | 5-phenyl-thiazol-2-yl | | + |
| 7 | H | 5-chloro-pyrazin-2-yl | | ++ |
| 8 | H | 2-(6-methyl-benzoxazolyl) | | +++ |
| 8a | H | 2-(6-methyl-benzoxazolyl) | | +++ |
| 8b | H | 2-(6-methyl-benzoxazolyl) | | + |
| 9 | H | thiazol-2-yl | 1058 | + |
| 10 | Me | thiazol-2-yl | | + |
| 11 | H | benzothiazol-2-yl | | +++ |
| 11a | H | benzothiazol-2-yl | | +++ |
| 11b | H | benzothiazol-2-yl | | + |

TABLE 1-continued

| Example Number | R | R₁ | FLIPR α7-HI (EC₅₀, nM) | FLIPR α7-HI (EC₅₀, nM) |
|---|---|---|---|---|
| 12 | Me | benzothiazol-2-yl | | ++ |
| 13 | H | 5-chloropyridin-2-yl | | + |
| 14 | Me | 5-chloropyridin-2-yl | | + |
| 15 | Me | isoquinolin-3-yl | 787 | ++ |
| 16 | H | 1H-benzimidazol-2-yl | 1286 | + |
| 17 | H | 5-chloropyrimidin-2-yl | 286 | ++ |
| 18 | Me | 5-chloropyrimidin-2-yl | | ++ |
| 19 | H | 5-methoxy-thiazolo[5,4-d]pyrimidin-2-yl | | + |
| 20 | H | 6-methoxypyrimidin-4-yl | 875 | ++ |
| 21 | Me | 6-methoxypyrimidin-4-yl | | ++ |
| 22 | Me | 5,6-dimethyl-1,2,4-triazin-3-yl | | NA |
| 23 | H | quinazolin-4-yl | | ++ |
| 24 | Me | quinazolin-4-yl | | + |
| 25 | H | 6-chloropyridazin-3-yl | | + |
| 26 | Me | 6-chloropyridazin-3-yl | | ++ |

TABLE 1-continued

| Example Number | R | R₁ | FLIPR α7-HI (EC₅₀, nM) | FLIPR α7-HI (EC₅₀, nM) |
|---|---|---|---|---|
| 27 | Me | quinazolin-2-yl | | + |
| 28 | H | 6-chlorothiazolo[5,4-b]pyridin-2-yl | | +++ |
| 28a | H | 6-chlorothiazolo[5,4-b]pyridin-2-yl | | +++ |
| 28b | H | 6-chlorothiazolo[5,4-b]pyridin-2-yl | | + |
| 29 | Me | 6-chlorothiazolo[5,4-b]pyridin-2-yl | | ++ |
| 30 | H | 6-bromothiazolo[4,5-b]pyrazin-2-yl | | NT |
| 31 | Me | 6-bromothiazolo[4,5-b]pyrazin-2-yl | | NT |
| 32 | H | thiazolo[4,5-b]pyrazin-2-yl | | ++ |
| 33 | Me | thiazolo[4,5-b]pyrazin-2-yl | | NT |
| 34 | H | [1,2,4]triazolo[1,5-a]pyridin-2-yl | | ++ |
| 35 | Me | [1,2,4]triazolo[1,5-a]pyridin-2-yl | | + |
| 36 | H | quinoxalin-2-yl | | ++ |

TABLE 1-continued

| Example Number | R | R₁ | FLIPR α7-HI (EC₅₀, nM) | FLIPR α7-HI (EC₅₀, nM) |
|---|---|---|---|---|
| 37 | H | imidazo[1,2-a]pyridin-2-yl | | + |
| 38 | H | 4-methoxy-thiazolo[5,4-d]pyrimidin-2-yl | | + |
| 39 | H | 6-benzyloxy-thiazolo[5,4-b]pyridin-2-yl | | NA |
| 40 | Me | quinolin-2-yl | 942 | ++ |
| 41 | H | 6-methyl-thiazolo[5,4-b]pyrazin-2-yl | | + |
| 42 | H | 6-oxo-5H-thiazolo[5,4-b]pyridin-2-yl | | ++ |
| 43 | H | 4,6-dimethyl-1,3,5-triazin-2-yl | | + |
| 44 | H | 6-fluoro-thiazolo[5,4-b]pyridin-2-yl | | ++ |
| 45 | Me | 6-fluoro-thiazolo[5,4-b]pyridin-2-yl | | + |
| 46 | H | 6-methoxy-thiazolo[5,4-b]pyridin-2-yl | | ++ |
| 47 | Me | 6-methoxy-thiazolo[5,4-b]pyridin-2-yl | | ++ |
| 48 | H | 6-dimethylamino-thiazolo[5,4-b]pyridin-2-yl | | + |

TABLE 1-continued
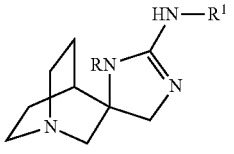
| Example Number | R | R₁ | FLIPR α7-HI (EC₅₀, nM) | FLIPR α7-HI (EC₅₀, nM) |
|---|---|---|---|---|
| 49 | H | 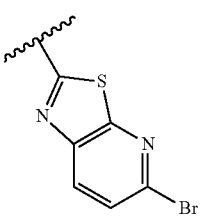 [SMILES: *c1nc2ccc(Br)nc2s1] |  | ++ |
| 50 | Me | 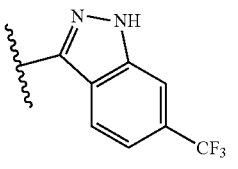 [SMILES: *c1n[nH]c2cc(C(F)(F)F)ccc12] |  | + |
| 51 | H | 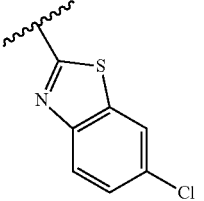 [SMILES: *c1nc2ccc(Cl)cc2s1] |  | NA |
| 52 | H | 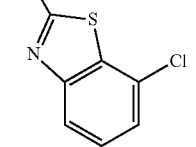 | 154 | ++ |
| 53 | H | 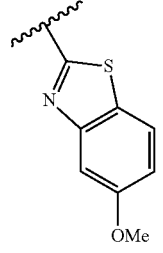 [SMILES: *c1nc2cc(OC)ccc2s1] |  | ++ |
| 54 | H | 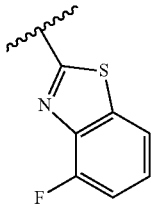 [SMILES: *c1nc2c(F)cccc2s1] |  | ++ |
| 55 | H | 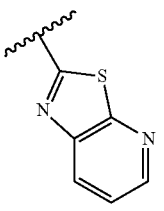 [SMILES: *c1nc2cccnc2s1] |  | +++ |
| 56 | H | 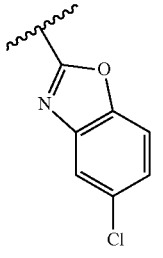 [SMILES: *c1nc2cc(Cl)ccc2o1] |  | +++ |
| 57 | H | (oxazole with Cl) |  | ++ |
| 58 | Me | 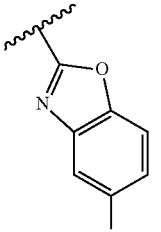 |  | ++ |
| 59 | H | 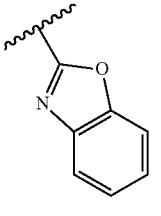 [SMILES: *c1nc2ccccc2o1] |  | +++ |

TABLE 1-continued

Structure: quinuclidine-fused imidazoline with RN and HN—R¹ substituents

| Example Number | R | R₁ | FLIPR α7-HI (EC₅₀, nM) | FLIPR α7-HI (EC₅₀, nM) |
|---|---|---|---|---|
| 60 | Me | benzoxazol-2-yl | | ++ |
| 61 | H | 6-(imidazol-1-yl)pyrimidin-4-yl | | ++ |
| 62 | H | 6-methyloxazolo[5,4-b]pyridin-2-yl | | ++ |
| 63 | H | 6-methylbenzothiazol-2-yl | | ++ |
| 64 | H | 7-methylpyrrolo[2,1-f][1,2,4]triazin-4-yl | | ++ |
| 65 | H | 7-chloropyrrolo[2,1-f][1,2,4]triazin-4-yl | | ++ |
| 66 | H | 7-bromopyrrolo[2,1-f][1,2,4]triazin-4-yl | | ++ |

TABLE 1-continued

ᵃActivity based on EC₅₀ nM values: +++ = <100 nM; ++ = 100-1000 nM; + = 1000-100000 nM.
ᵇNT = Not tested;
NA = Not active (>1000000 nM).

TABLE 2

Structure: quinuclidine-fused oxazoline with HN—R¹ substituent

| Example Number | R₁ | FLIPR α7-HI (EC₅₀, nM) | FLIPR α7-HI (EC₅₀, nM) |
|---|---|---|---|
| 67 | 6-methoxybenzothiazol-2-yl | | + |
| 68 | 5-phenylthiazol-2-yl | | ++ |
| 69 | 7-chloropyrrolo[2,1-f][1,2,4]triazin-4-yl | | + |

ᵃActivity based on EC₅₀ nM values: +++ = <100 nM; ++ = 100-1000 nM; + = 1000-100000 nM.
ᵇNT = Not tested; NA = Not active (>1000000 nM).

TABLE 3

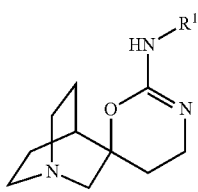

| Example Number | R₁ | FLIPR α7-HI (EC$_{50}$, nM) | FLIPR α7-HI (EC$_{50}$, nM) |
|---|---|---|---|
| 70 | 6-methoxy-benzothiazol-2-yl | | ++ |
| 71 | 5-phenyl-thiazol-2-yl | 87 | +++ |
| 72 | 5-chloro-pyrazin-2-yl | | + |
| 73 | thiazol-2-yl | 4533 | + |
| 74 | benzothiazol-2-yl | | ++ |
| 75 | 5-chloro-pyridin-2-yl | | + |
| 76 | isoquinolin-3-yl | 264 | ++ |

TABLE 3-continued

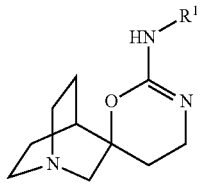

| Example Number | R₁ | FLIPR α7-HI (EC$_{50}$, nM) | FLIPR α7-HI (EC$_{50}$, nM) |
|---|---|---|---|
| 76a | isoquinolin-3-yl | | ++ |
| 76b | isoquinolin-3-yl | | NA |
| 77 | 1H-benzimidazol-2-yl | >100000 | NA |
| 78 | 5-chloro-pyrimidin-2-yl | | + |
| 79 | methoxy-thiazolo-pyrimidinyl | | + |
| 80 | 6-methoxy-pyrimidin-4-yl | 3647 | + |

TABLE 3-continued

| Example Number | R₁ | FLIPR α7-HI (EC₅₀, nM) | FLIPR α7-HI (EC₅₀, nM) |
|---|---|---|---|
| 81 | 3-(4,6-dimethyl-1,2,4-triazin-3-yl) |  | + |
| 82 | quinazolin-4-yl |  | ++ |
| 83 | 6-chloropyridazin-3-yl |  | + |
| 84 | quinazolin-2-yl |  | ++ |
| 85 | quinoxalin-2-yl |  | + |
| 86 | quinolin-2-yl | 1807 | + |
| 87 | 5-bromothiazolo[5,4-b]pyridin-2-yl |  | + |
| 88 | 7-chloropyrrolo[2,1-f][1,2,4]triazin-4-yl |  | + |

[a] Activity based on EC₅₀ nM values; +++ = <100 nM; ++ = 100-1000 nM; + = 1000-100000 nM.
[b] NT = Not tested; NA = Not active (>1000000 nM).

TABLE 4

| Example Number | R₁ | FLIPR α7-HI (EC₅₀, nM) | FLIPR α7-HI (EC₅₀, nM) |
|---|---|---|---|
| 89 | 6-methoxybenzothiazol-2-yl |  | NA |

TABLE 4-continued

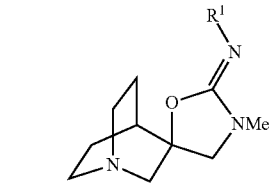

| Example Number | $R_1$ | FLIPR α7-HI (EC$_{50}$, nM) | FLIPR α7-HI (EC$_{50}$, nM) |
|---|---|---|---|
| 90 | 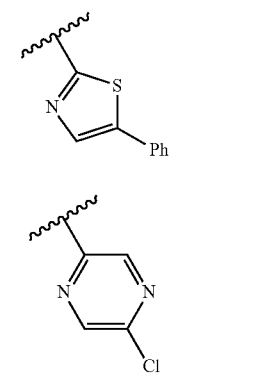 | | ++ |
| 91 | | | + |

$^a$Activity based on EC$_{50}$ nM values: +++ = <100 nM; ++ = 100-1000 nM; + = 1000-100000 nM.
$^b$NT = Not tested; NA = Not active (>1000000 nM).

Pharmaceutical Compositions and Methods of Treatment

Compounds of formula I bind to alpha 7 and can be useful in treating affective disorders and neurodegenerative disorders. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of affective disorders or neuro degenerative disorders.

Another aspect of the invention is the use of a compound of formula I in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

DESCRIPTION OF SPECIFIC EMBODIMENTS $^1$H-NMR spectra were run on a Bruker 500, 400, or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a Phenomenex-Luna 4.6×50 mm S 10 reverse phase column employing a flow rate of 4 mL/min using a 0.1% TFA in methanol/water gradient [0-100% in 3 min, with 4 min run time] and a UV detector set at 220 nm or Gemini C18 4.6×50 mm 5u reverse phase column employing a flow rate of 5 mL/min using a 10 mM ammonium acetate acetonitrile/water gradient [5-95% in 3 min, with 4 min run time] and a UV detector set at 220 nm (negative-ion mass spectrometry). Unless otherwise stated, purification could be done by preparative C-18 column employing gradients of methanol-water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient.

EXAMPLE 1

N-(6-Methoxy-1,3-benzothiazol-2-yl)-1',5'-dihydrospiro[4-azabicyclo[2.2.2]octane-2,4'-imidazol]-2'-amine

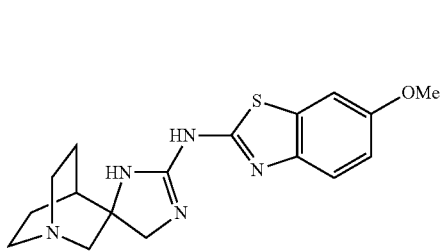 [SMILES: COc1ccc2nc(NC3=NCC4(CN5CCC4CC5)N3)sc2c1]

Step A: N-(6-Methoxybenzo[d]thiazol-2-yl)-1H-imidazole-1-carbothioamide

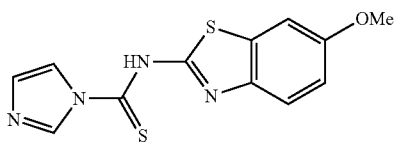 [SMILES: COc1ccc2nc(NC(=S)n3ccnc3)sc2c1]

To 6-methoxybenzo[d]thiazol-2-amine (0.53 g, 2.9 mmol) in acetonitrile (20 mL) was added 1,1'-thiocarbonyldiimidazole (0.68 g, 3.8 mmol). The reaction mixture was stirred at 65° C. for 24 h. The precipitate was filtered and washed with acetonitrile (2×20 mL) to yield the product. The product was taken directly to the next step without any further purification or characterization.

Step B: N-(6-Methoxy-1,3-benzothiazol-2-yl)-1',5'-dihydrospiro[4-azabicyclo[2.2.2]octane-2,4'-imidazol]-2'-amine

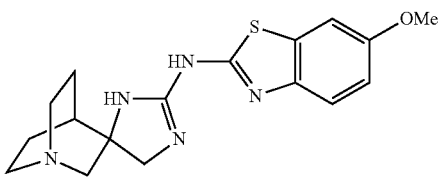 [SMILES: COc1ccc2nc(NC3=NCC4(CN5CCC4CC5)N3)sc2c1]

To 3-(aminomethyl)quinuclidin-3-amine (0.150 g, 0.966 mmol) in N,N-dimethylformamide (3.2 mL) was added N-(6-methoxybenzo[d]thiazol-2-yl)-1H-imidazole-1-carbothioamide (0.337 g, 1.16 mmol). The suspension was placed into a preheated oil-bath and stirred at 85° C. for 3 h. N,N'-diisopropylcarbodiimide (0.452 mL, 2.90 mmol) was then added and the mixture was stirred at 85° C. for 16 h. The mixture was concentrated and purified by silica gel chromatography (0-30% 9:1 methanol:ammonium hydroxide-chloroform) followed by purification by reverse phase preparatory HPLC (0-100% TFA-methanol-water). The product fractions were combined and concentrated in vacuo to afford N-(6-methoxy-1,3-benzothiazol-2-yl)-1',5'-dihydrospiro[4-azabicyclo[2.2.2]octane-2,4'-imidazol]-2'-amine as the trifluoroacetic acid salt (74 mg, 0.16 mmol, 17% yield) as a white solid. $^1$H NMR (400 MHz, DMSO-$d_6$) δ ppm 9.89 (1H, br. s.), 9.12 (1H, br. s.), 8.82 (1H, br. s.), 7.54 (1H, d, J=8.8 Hz), 7.48 (1H, d, J=2.5 Hz), 7.01 (1H, dd, J=8.9, 2.6 Hz), 3.92 (1H, d, J=10.8 Hz), 3.75-3.83 (4H, m), 3.63 (1H, d, J=13.8 Hz), 3.46 (1H, d, J=13.8 Hz), 3.17-3.39 (3H, m), 2.07-2.26 (2H, m), 1.81-2.01 (3H, m). MS (LC/MS) R.T.=0.98; [M+H]$^+$=344.19.

The compounds in Table 5 were synthesized according to the method of Example 1 using the appropriate commercially available amine.

TABLE 5

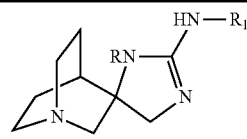

| Example Number | R | R$_1$ | LCMS RT (min) | LCMS Ion [M + H]$^+$ | $^1$H NMR |
|---|---|---|---|---|---|
| 2 | Me | ![benzothiazole-OMe] | 1.06 | 357.97 | $^1$H NMR (400 MHz, DMSO-$d_6$) δ ppm 10.02 (1 H, br. s.), 8.65 (1 H, br. s.), 7.47 (1 H, d, J = 8.8 Hz), 7.42 (1 H, d, J = 2.5 Hz), 6.96 (1 H, dd, J = 8.8, 2.8 Hz), 3.81-3.88 (1 H, m), 3.79 (3 H, s), 3.70-3.76 (1 H, m), 3.40-3.63 (3 H, m), 3.24-3.38 (3 H, m), 3.13 (3 H, s), 2.18-2.36 (2 H, m), 1.78-2.09 (3 H, m) |
| 3 | Et | ![benzothiazole-OMe] | 0.82 | 372.12 | $^1$H NMR (400 MHz, DMSO-$d_6$) δ ppm 9.99 (1 H, br. s.), 8.59 (1 H, br. s.), 7.47 (1 H, d, J = 8.8 Hz), 7.41 (1 H, d, J = 2.8 Hz), 6.95 (1 H, dd, J = 8.8, 2.5 Hz), 3.73-3.84 (5 H, m), 3.47-3.73 (3 H, m), 3.23-3.46 (4 H, m), 2.26-2.32 (1 H, m), 2.09-2.21 (1 H, m), 1.78-2.05 (4 H, m), 1.21 (3 H, t, J = 7.0 Hz) |

TABLE 5-continued

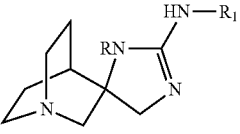

| Example Number | R | R₁ | LCMS RT (min) | LCMS Ion [M + H]⁺ | ¹H NMR |
|---|---|---|---|---|---|
| 4 | H | 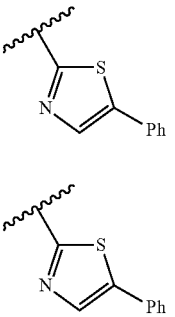 | 1.22 | 340.21 | ¹H NMR (400 MHz, DMSO-d₆) δ ppm 9.97 (1 H, br. s.), 9.37 (1 H, br. s.), 8.81 (1 H, br. s.), 8.00 (2 H, d, J = 7.3 Hz), 7.62 (1 H, s), 7.45 (2 H, t, J = 7.5 Hz), 7.32-7.40 (1 H, m), 3.93-4.03 (1 H, m), 3.80-3.89 (1 H, m), 3.61-3.71 (1 H, m), 3.49-3.60 (1 H, m), 3.19-3.41 (4 H, m), 2.22-2.30 (1 H, m), 2.06-2.20 (1 H, m), 1.85-2.00 (3 H, m) |
| 5 | Me | 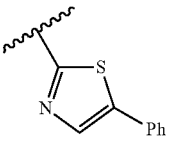 [SMILES: *c1ncc(-c2ccccc2)s1] | 1.15 | 353.95 | ¹H NMR (400 MHz, DMSO-d₆) δ ppm 10.01 (1 H, br. s.), 8.53 (1 H, br. s.), 7.91-7.99 (2 H, m), 7.38-7.46 (3 H, m), 7.28-7.37 (1 H, m), 3.81-3.89 (1 H, m), 3.71-3.79 (1 H, m), 3.41-3.63 (3 H, m), 3.25-3.39 (3 H, m), 3.14 (3 H, s), 2.19-2.37 (2 H, m), 1.79-2.09 (3 H, m) |
| 6 | Et | 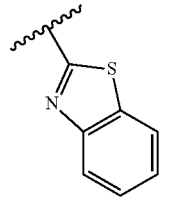 [SMILES: *c1nc2ccccc2s1] | 0.86 | 368.15 | ¹H NMR (400 MHz, DMSO-d₆) δ ppm 10.03 (1 H, br. s.), 8.48 (1 H, br. s.), 7.93-7.99 (2 H, m), 7.37-7.47 (3 H, m), 7.27-7.37 (1 H, m), 3.76-3.85 (2 H, m), 3.48-3.73 (3 H, m), 3.22-3.46 (5 H, m), 2.28-2.34 (1 H, m), 2.09-2.23 (1 H, m), 1.81-2.08 (3 H, m), 1.22 (3 H, t, J = 6.9 Hz) |
| 11 | H | 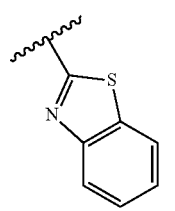 [SMILES: *c1nc2ccccc2s1] | 0.83 | 314.10 | ¹H NMR (400 MHz, DMSO-d₆) δ ppm 9.81 (1 H, br. s.), 8.97 (1 H, br. s.), 8.74 (1 H, br. s.), 7.82 (1 H, d, J = 7.8 Hz), 7.59 (1 H, d, J = 8.0 Hz), 7.38 (1 H, t, J = 7.7 Hz), 7.22 (1 H, t, J = 7.5 Hz), 3.92 (1 H, d, J = 10.5 Hz), 3.78 (1 H, d, J = 10.5 Hz), 3.62 (1 H, d, J = 13.8 Hz), 3.44 (1 H, d, J = 13.8 Hz), 3.19-3.37 (4 H, m), 2.07-2.23 (2 H, m), 1.84-2.01 (3 H, m) |
| 11aᵃ | H | 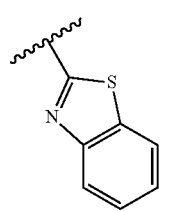 [SMILES: *c1nc2ccccc2s1] | 0.67 | 314.08 | ¹H NMR (400 MHz, DMSO-d₆) δ ppm 9.81 (1 H, br. s.), 8.97 (1 H, br. s.), 8.74 (1 H, br. s.), 7.82 (1 H, d, J = 7.8 Hz), 7.59 (1 H, d, J = 8.0 Hz), 7.38 (1 H, t, J = 7.7 Hz), 7.22 (1 H, t, J = 7.5 Hz), 3.92 (1 H, d, J = 10.5 Hz), 3.78 (1 H, d, J = 10.5 Hz), 3.62 (1 H, d, J = 13.8 Hz), 3.44 (1 H, d, J = 13.8 Hz), 3.19-3.37 (4 H, m), 2.07-2.23 (2 H, m), 1.84-2.01 (3 H, m) |
| 11bᵃ | H | 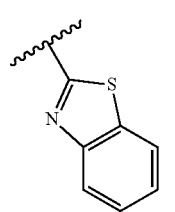 [SMILES: *c1nc2ccccc2s1] | 0.67 | 314.07 | ¹H NMR (400 MHz, DMSO-d₆) δ ppm 9.81 (1 H, br. s.), 8.97 (1 H, br. s.), 8.74 (1 H, br. s.), 7.82 (1 H, d, J = 7.8 Hz), 7.59 (1 H, d, J = 8.0 Hz), 7.38 (1 H, t, J = 7.7 Hz), 7.22 (1 H, t, J = 7.5 Hz), 3.92 (1 H, d, J = 10.5 Hz), 3.78 (1 H, d, J = 10.5 Hz), 3.62 (1 H, d, J = 13.8 Hz), 3.44 (1 H, d, J = 13.8 Hz), 3.19-3.37 (4 H, m), 2.07-2.23 (2 H, m), 1.84-2.01 (3 H, m) |
| 12 | Me | | 0.80 | 328.12 | ¹H NMR (400 MHz, DMSO-d₆) δ ppm 9.97 (1 H, br. s.), 8.71 (1 H, br. s.), 7.78 (1 H, d, J = 7.8 Hz), 7.56 (1 H, d, J = 8.0 Hz), 7.34 (1 H, t, J = 7.5 Hz), 7.18 (1 H, t, J = 7.5 Hz), 3.82-3.88 (1 H, m), 3.75 (1 H, d, J = 10.0 Hz), 3.41-3.69 (3 H, m), 3.22-3.38 (3 H, m), 3.15 (3 H, s), 2.19-2.39 (2 H, m), 1.78-2.11 (3 H, m) |

TABLE 5-continued

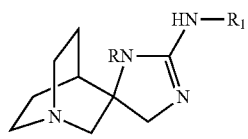

| Example Number | R | R₁ | LCMS RT (min) | LCMS Ion [M + H]⁺ | ¹H NMR |
|---|---|---|---|---|---|
| 16 | H | 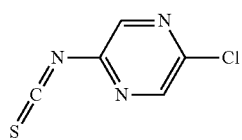 | 0.40 | 297.15 | ¹H NMR (400 MHz, MeOD) δ ppm 7.35-7.42 (2 H, m), 7.26-7.33 (2 H, m), 4.01 (1 H, d, J = 10.8 Hz), 3.81 (1 H, d, J = 10.8 Hz), 3.72 (1 H, dd, J = 14.1, 2.5 Hz), 3.53 (1 H, dd, J = 13.9, 2.1 Hz), 3.34-3.47 (4 H, m), 2.22-2.37 (2 H, m), 2.01-2.16 (3 H, m) |

ᵃThe enantiomers were spared using a Chiralpak OD-H (4.6 × 250 mm, 5 μm) column with a mobile phase consisting of 35% methanol (0.1% DEA) in CO₂. The wavelength was set at 215 nM. The separated peaks were concentrated in vacuo to yield white solids.

EXAMPLE 7

N-(5-Chloro-2-pyrazinyl)-1',5'-dihydrospiro[4-azabicyclo[2.2.2]octane-2,4'-imidazol]-2'-amine

Step A: 2-Chloro-5-isothiocyanatopyrazine

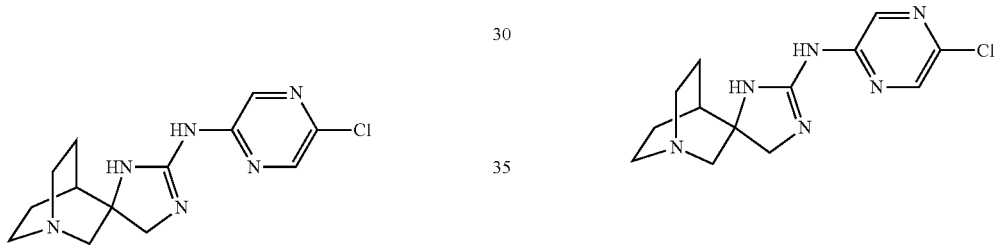

A solution of 5-chloropyrazin-2-amine (13.0 g, 100 mmol) and 1,1'-thiocarbonyldipyridin-2 (1H)-one (27.9 g, 120 mmol) was stirred in DCM (200 mL) at room temperature for 1 h. The reaction was concentrated to ca. 100 mL volume and filtered through a pad of silica gel (1 L), washing with ethyl acetate in hexanes (10%). The filtrate was concentrated and dried to afford 2-chloro-5-isothiocyanatopyrazine (14.3 g, 83.0 mmol, 83% yield). ¹H NMR (400 MHz, chloroform-d) δ ppm 8.38 (d, J=1.26 Hz, 1H) 8.18 (d, J=1.26 Hz, 1H). MS (LC/MS) R.T.=1.84; [M+H]⁺=172.09.

Step B: N-(5-Chloro-2-pyrazinyl)-1',5'-dihydrospiro[4-azabicyclo[2.2.2]octane-2,4'-imidazol]-2'-amine To 3-(aminomethyl)quinuclidin-3-amine (0.110 g, 0.709 mmol) in N,N-dimethylformamide (2.4 mL) was added 2-chloro-5-isothiocyanatopyrazine (0.134 g, 0.779 mmol). The suspension was placed into a preheated oil-bath and stirred at 70° C. for 16 h. N,N'-diisopropylcarbodiimide (0.331 mL, 2.13 mmol) was then added and the mixture was stirred at 85° C. for 16 h. The mixture was concentrated and purified by silica gel chromatography (0-30% 9:1 methanol ammonium hydroxide-chloroform) followed by purification by reverse phase preparatory HPLC (0-100% TFA-methanol-water). The product fractions were combined and concentrated in vacuo to afford N-(5-chloro-2-pyrazinyl)-1',5'-dihydrospiro[4-azabicyclo[2.2.2]octane-2,4'-imidazol]-2'-amine as the trifluoroacetic acid salt (35 mg, 0.11 mmol, 15% yield) as a clear oil. ¹H NMR (400 MHz, DMSO-d₆) δ ppm 10.15 (2H, br. s.), 9.46 (1H, br. s.), 8.52 (1H, d, J=1.3 Hz), 8.29 (1H, d, J=1.5 Hz), 4.02 (1H, d, J=11.3 Hz), 3.89 (1H, d, J=11.0 Hz), 3.62 (2H, d, J=14.3 Hz), 3.15-3.42 (4H, m), 2.27 (1H, d, J=2.8 Hz), 2.04-2.17 (1H, m), 1.82-2.04 (3H, m). MS (LC/MS) R.T.=0.68; [M+H]⁺=293.06.

The compounds in Table 6 were synthesized according to the method of Example 7 using the appropriate commercially available amine.

TABLE 6

| Example Number | R | R₁ | LCMS RT (min) | LCMS Ion [M + H]⁺ | ¹H NMR |
|---|---|---|---|---|---|
| 9 | H | 2-thiazolyl | 0.23 | 264.08 | ¹H NMR (400 MHz, MeOD) δ ppm 7.45 (1 H, d, J = 4.0 Hz), 7.22 (1 H, d, J = 4.0 Hz), 4.15 (1 H, d, J = 11.0 Hz), 3.91 (1 H, d, J = 11.0 Hz), 3.61-3.75 (2 H, m), 3.34-3.52 (4 H, m), 2.36-2.42 (1 H, m), 2.22-2.33 (1 H, m), 2.03-2.15 (3 H, m) |
| 10 | Me | 2-thiazolyl | 0.23 | 278.11 | ¹H NMR (400 MHz, DMSO-d₆) δ ppm 10.41 (1 H, br. s.), 8.59 (1 H, br. s.), 7.47 (1 H, d, J = 4.0 Hz), 7.20 (1 H, d, J = 4.3 Hz), 3.85 (1 H, d, J = 8.0 Hz), 3.76 (1 H, d, J = 8.0 Hz), 3.41-3.68 (3 H, m), 3.22-3.40 (3 H, m), 3.15 (3 H, s), 2.33 (1 H, t, J = 2.9 Hz), 2.16-2.28 (1 H, m), 1.77-2.12 (3 H, m) |
| 13 | H | 5-chloropyridin-2-yl | 0.59 | 292.11 | ¹H NMR (400 MHz, MeOD) δ ppm 8.38 (1 H, d, J = 2.5 Hz), 7.91 (1 H, dd, J = 8.8, 2.5 Hz), 7.14 (1 H, d, J = 8.8 Hz), 4.18 (1 H, d, J = 11.0 Hz), 3.94 (1 H, d, J = 11.0 Hz), 3.70 (2 H, s), 3.36-3.57 (4 H, m), 2.36-2.44 (1 H, m), 2.23-2.35 (1 H, m), 2.02-2.18 (3 H, m) |
| 14 | Me | 5-chloropyridin-2-yl | 0.37 | 306.12 | ¹H NMR (400 MHz, DMSO-d₆) δ ppm 10.89 (1 H, br. s.), 10.29 (1 H, br. s.), 9.78 (1 H, br. s.), 8.39 (1 H, d, J = 2.5 Hz), 8.07 (1 H, dd, J = 8.8, 2.5 Hz), 7.45 (1 H, d, J = 8.5 Hz), 4.04 (1 H, d, J = 11.0 Hz), 3.84 (1 H, d, J = 11.0 Hz), 3.73 (1 H, d, J = 14.8 Hz), 3.44-3.62 (2 H, m), 3.22-3.41 (6 H, m), 2.36-2.43 (1 H, m), 1.99-2.22 (2 H, m), 1.79-1.99 (2 H, m) |
| 15 | Me | isoquinolin-3-yl | 0.77 | 322.12 | ¹H NMR (400 MHz, DMSO-d₆) δ ppm 10.85 (1 H, br. s.), 10.32 (1 H, br. s.), 9.83 (1 H, br. s.), 9.26 (1 H, s), 8.24 (1 H, d, J = 8.0 Hz), 8.02 (1 H, d, J = 8.3 Hz), 7.83 (1 H, t, J = 7.5 Hz), 7.79 (1 H, s), 7.67 (1 H, t, J = 7.5 Hz), 4.06 (1 H, d, J = 10.5 Hz), 3.86 (1 H, d, J = 10.8 Hz), 3.77 (1 H, d, J = 14.8 Hz), 3.47-3.64 (2 H, m), 3.25-3.42 (6 H, m), 2.38-2.46 (1 H, m), 2.01-2.24 (2 H, m), 1.81-2.00 (2 H, m) |
| 17ᵃ | H | 5-chloropyrimidin-2-yl | 0.29 | 293.17 | ¹H NMR (400 MHz, MeOD) δ ppm 8.43 (2 H, s), 3.86 (1 H, d, J = 10.0 Hz), 3.52 (1 H, d, J = 9.8 Hz), 3.01-3.14 (2 H, m), 2.71-2.98 (4 H, m), 1.91-2.05 (2 H, m), 1.62-1.88 (3 H, m) |
| 18 | Me | 5-chloropyrimidin-2-yl | 0.22 | 307.14 | ¹H NMR (400 MHz, DMSO-d₆) δ ppm 10.30 (1 H, br. s.), 9.56 (1 H, br. s.), 8.85 (2 H, s), 4.01 (1 H, d, J = 11.0 Hz), 3.84 (1 H, d, J = 11.0 Hz), 3.72 (1 H, d, J = 14.8 Hz), 3.43-3.60 (2 H, m), 3.23-3.41 (6 H, m), 2.34-2.41 (1 H, m), 1.98-2.19 (2 H, m), 1.80-1.98 (2 H, m) |
| 22 | Me | 5,6-dimethyl-1,2,4-triazin-3-yl | 0.18 | 302.25 | ¹H NMR (400 MHz, MeOD) δ ppm 4.10 (1 H, d, J = 10.8 Hz), 3.88 (1 H, d, J = 11.0 Hz), 3.77 (1 H, dd, J = 14.3, 2.3 Hz), 3.63 (1 H, dd, J = 14.3, 2.3 Hz), 3.53-3.59 (1 H, m), 3.29-3.53 (6 H, m), 2.68 (3 H, s), 2.54 (3 H, s), 2.36-2.50 (2 H, m), 1.97-2.27 (3 H, m) |
| 25 | H | 6-chloropyridazin-3-yl | 0.27 | 293.17 | ¹H NMR (400 MHz, MeOD) δ ppm 7.85 (1H, d, J = 9.3 Hz), 7.50 (1 H, d, J = 9.3 Hz), 4.22 (1 H, d, J = 11.3 Hz), 3.98 (1 H, d, J = 11.3 Hz), 3.67-3.75 (2 H, m), 3.45-3.54 (2 H, m), 3.33-3.44 (2 H, m), 2.39-2.46 (1 H, m), 2.26-2.39 (1 H, m), 2.00-2.20 (3 H, m) |

TABLE 6-continued

| Example Number | R | R₁ | LCMS RT (min) | LCMS Ion [M + H]⁺ | ¹H NMR |
|---|---|---|---|---|---|
| 26[a] | Me | 3-yl-6-chloropyridazine | 0.21 | 307.21 | ¹H NMR (400 MHz, DMSO-d₆) δ ppm 8.40 (1 H, br. s.), 7.47 (1 H, d, J = 9.3 Hz), 7.00 (1 H, d, J = 9.0 Hz), 3.75 (1 H, d, J = 8.8 Hz), 3.44 (1 H, d, J = 10.0 Hz), 3.12 (3 H, s), 3.03 (1 H, d, J = 14.6 Hz), 2.74-2.96 (3 H, m), 2.70 (2 H, t, J = 7.8 Hz), 1.89-2.05 (2 H, m), 1.68-1.84 (1 H, m), 1.41-1.58 (2 H, m) |
| 27 | Me | quinazolin-2-yl | 0.50 | 323.28 | ¹H NMR (400 MHz, MeOD) δ ppm 9.53 (1 H, s), 8.14 (1 H, d, J = 7.5 Hz), 8.00-8.09 (1 H, m), 7.87-7.98 (1 H, m), 7.69 (1 H, t, J = 7.5 Hz), 4.25 (1 H, d, J = 10.8 Hz), 3.96-4.00 (1 H, m), 3.87 (1 H, dd, J = 14.8, 1.8 Hz), 3.63-3.71 (1 H, m), 3.38-3.63 (7 H, m), 2.51-2.59 (1 H, m), 2.33-2.51 (1 H, m), 2.00-2.33 (3 H, m) |
| 34[b] | H | [1,2,4]triazolo[1,5-a]pyridin-2-yl | 0.39 | 298.25 | ¹H NMR (500 MHz, DMSO-d₆) δ ppm 10.27 (1 H, br. s.), 10.14 (1 H, br. s.), 9.27 (1 H, br. s.), 8.90 (1 H, d, J = 6.7 Hz), 7.77 (2 H, d, J = 3.7 Hz), 7.28 (1 H, dt, J = 6.7, 4.1 Hz), 4.02 (1 H, d, J = 11.0 Hz), 3.90 (1 H, d, J = 10.7 Hz), 3.55-3.69 (2 H, m), 3.13-3.41 (4 H, m), 2.22-2.33 (1 H, m), 2.05-2.19 (1 H, m), 1.82-2.04 (3 H, m) |
| 35[b,c] | Me | [1,2,4]triazolo[1,5-a]pyridin-2-yl | 0.73 | 312.3 | ¹H NMR (500 MHz, DMSO-d₆) δ ppm 8.61 (1 H, d, J = 6.7 Hz), 7.82 (1 H, br. s.), 7.44-7.50 (2 H, m), 6.95 (1 H, ddd, J = 6.6, 5.0, 3.4 Hz), 3.65-3.71 (1 H, m), 3.35-3.44 (1 H, m), 3.07 (3 H, s), 2.97-3.03 (1 H, m), 2.83-2.93 (1 H, m), 2.73-2.83 (2 H, m), 2.66-2.72 (2 H, m), 1.93-2.04 (1 H, m), 1.88-1.93 (1 H, m), 1.68-1.78 (1 H, m), 1.41-1.56 (2 H, m) |
| 36 | H | quinoxalin-2-yl | 0.64 | 309.23 | ¹H NMR (400 MHz, MeOD) δ ppm 8.70 (1 H, s), 8.09 (1 H, d, J = 8.3 Hz), 8.05 (1 H, d, J = 8.3 Hz), 7.78-7.86 (1 H, m), 7.70-7.78 (1 H, m), 4.28 (1 H, d, J = 11.0 Hz), 4.07 (1 H, d, J = 11.3 Hz), 3.71-3.81 (2 H, m), 3.47-3.56 (2 H, m), 3.36-3.44 (2 H, m), 2.42-2.47 (1 H, m), 2.30-2.42 (1 H, m), 2.05-2.19 (3 H, m) |
| 37 | H | imidazo[1,2-a]pyridin-2-yl | 0.32 | 297.24 | ¹H NMR (400 MHz, MeOD) δ ppm 8.41 (1 H, d, J = 6.8 Hz), 7.56 (1 H, d, J = 9.3 Hz), 7.37 (1 H, dd, J = 8.5, 7.3 Hz), 6.99 (1 H, app t, J = 6.8 Hz), 4.16 (1 H, d, J = 10.8 Hz), 3.92 (1 H, d, J = 10.8 Hz), 3.64-3.77 (2 H, m), 3.44-3.52 (2 H, m), 3.34-3.43 (3 H, m), 2.38-2.45 (1 H, m), 2.24-2.37 (1 H, m), 2.03-2.19 (3 H, m) |
| 40 | Me | quinolin-2-yl | 0.62 | 322.24 | ¹H NMR (400 MHz, DMSO-d₆) δ ppm 10.93 (1 H, br. s.), 10.47 (1 H, br. s.), 10.16-10.34 (1 H, m), 8.42-8.51 (1 H, m), 8.17 (1 H, br. s.), 7.95-8.03 (1 H, m), 7.77-7.86 (1 H, m), 7.47-7.65 (2 H, m), 4.00-4.20 (1 H, m), 3.84-3.97 (1 H, m), 3.68-3.83 (1 H, m), 3.57-3.68 (1 H, m), 3.46-3.57 (1 H, m), 3.22-3.46 (6 H, m), 2.39-2.47 (1 H, m), 2.14-2.27 (1 H, m), 2.02-2.14 (1 H, m), 1.81-2.02 (2 H, m) |

TABLE 6-continued

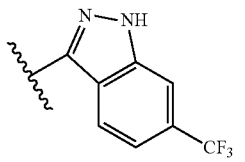

| Example Number | R | R₁ | LCMS RT (min) | LCMS Ion [M + H]⁺ | ¹H NMR |
|---|---|---|---|---|---|
| 51[c] | H | 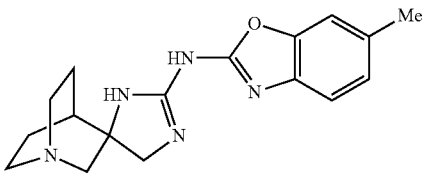 | 1.19 | 365.12 | ¹H NMR (400 MHz, MeOD) δ ppm 8.43 (1 H, d, J = 8.5 Hz), 8.08 (1 H, s), 7.83 (1 H, d, J = 8.5 Hz), 4.23 (1 H, d, J = 11.0 Hz), 4.01 (1 H, d, J = 11.0 Hz), 3.40-3.57 (5 H, m), 2.30-2.52 (2 H, m), 2.00-2.21 (4 H, m) |

[a]Following HPLC purification, the free amine was isolated using an MCX cartridge with 2.0 M ammonia in methanol.
[b]Amine synthesized according to Vercek, B.; et al. Monatshefte fuer Chemie 1983, 114, 789-98.
[c]The free base was isolated after silica gel column chromatography.

EXAMPLE 8

N-(6-Methyl-1,3-benzoxazol-2-yl)-1',5'-dihydrospiro[4-azabicyclo[2.2.2]octane-2,4'-imidazol]-2'-amine

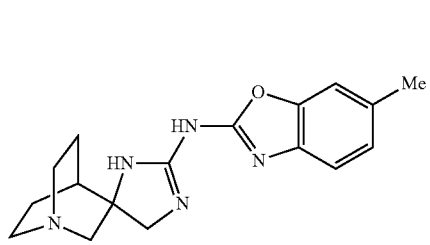

Step A: 6-Methylbenzo[d]oxazol-2-amine

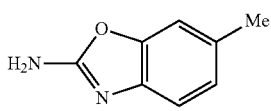 [SMILES: Cc1ccc2nc(N)oc2c1]

An oven-dried, round-bottomed flask was charged with di(1H-imidazol-1-yl)methanimine (1.40 g, 8.69 mmol), 2-amino-5-methylphenol (713 mg, 5.79 mmol) and anhydrous THF (20 ml) at ambient temperature. The resulting suspension was refluxed under N₂ (g) for 2 h to give complete conversion based on LC/MS. The solvent was removed in vacuo and the residue was purified by silica gel chromatography (0-30% 9:1 methanol:ammonium hydroxide-chloroform) to afford the expected product, benzo[d]oxazol-2-amine (792 mg, 5.35 mmol, 92% yield), as a grey solid. ¹H NMR (400 MHz, CHLOROFORM-d) δ ppm 7.19-7.34 (1H, m), 7.11 (1H, s), 7.01 (1H, d, J=7.8 Hz), 5.60 (2H, br. s.), 2.43 (3H, s). MS (LC/MS) R.T.=0.89; [M+H]⁺=149.09.

Step B: Dimethyl 6-methylbenzo[d]oxazol-2-ylcarbonimidodithioate

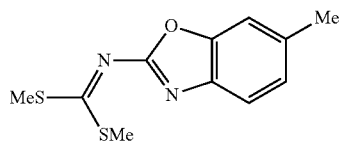 [SMILES: CSC(=Nc1nc2ccc(C)cc2o1)SC]

To a suspension of 6-methylbenzo[d]oxazol-2-amine (200 mg, 1.35 mmol) in DMF (1.4 mL) was added 20.0 M sodium hydroxide (135 µL, 2.70 mmol). The mixture was allowed to stir 10 min at room temperature before carbon disulfide was added (203 µL, 3.37 mmol) and the mixture was stirred for 10 min. An additional portion of 20.0 M sodium hydroxide (135 µL, 2.70 mmol) was added and the mixture was again stirred for 10 min. Finally, iodomethane (203 µL, 3.24 mmol) was added dropwise. An exotherm was noticed during this addition. The mixture was stirred for 15 min, at which time a voluminous precipitate had formed. The mixture was poured into water and the solids were collected by filtration, washed with water, and dried to afford dimethyl 6-methylbenzo[d]oxazol-2-ylcarbonimidodithioate (289 mg, 1.14 mmol, 85% yield) as a brown solid. MS (LC/MS) R.T.=1.88; [M+H]⁺=252.95.

Step C: N-(6-Methyl-1,3-benzoxazol-2-yl)-1',5'-dihydrospiro[4-azabicyclo[2.2.2]octane-2,4'-imidazol]-2'-amine

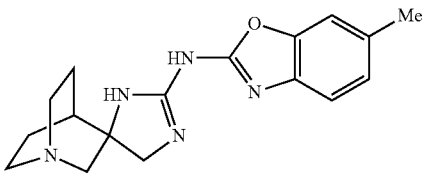 [SMILES: Cc1ccc2nc(NC3=NCC4(CN5CCC4CC5)N3)oc2c1]

To 3-(aminomethyl)quinuclidin-3-amine (0.132 g, 0.848 mmol) in N,N-dimethylformamide (2.0 mL) was added dimethyl 6-methylbenzo[d]oxazol-2-ylcarbonimidodithioate (0.214 g, 0.848 mmol). The suspension was stirred at ambient temperature for 24 h. The mixture was concentrated and purified by reverse phase preparatory HPLC (0-100% TFA-methanol-water). The product fractions were combined and concentrated in vacuo to afford N-(6-methyl-1,3-benzoxazol-2-yl)-1',5'-dihydrospiro[4-azabicyclo[2.2.2]octane-2,4'-imidazol]-2'-amine as the trifluoroacetic acid salt (107 mg, 0.216 mmol, 86% yield) as a tan solid. $^1$H NMR (400 MHz, DMSO-$d_6$) δ ppm 10.09 (1H, br. s.), 9.05 (1H, br. s.), 8.63 (1H, br. s.), 7.23-7.34 (2H, m), 7.09 (1H, d, J=7.8 Hz), 3.91 (1H, d, J=10.5 Hz), 3.79 (1H, d, J=10.8 Hz), 3.64 (1H, d, J=13.8 Hz), 3.42 (1H, d, J=13.8 Hz), 3.17-3.35 (4H, m), 2.34-2.43 (3H, m), 2.09-2.23 (2H, m), 1.79-2.01 (3H, m). MS (LC/MS) R.T.=0.92; [M+H]$^+$=312.24.

The compounds in Table 7 were synthesized according to the method of Example 8 using the appropriate commercially available amine

TABLE 7

| Example Number | R | R$_1$ | LCMS RT (min) | LCMS Ion [M + H]$^+$ | $^1$H NMR |
|---|---|---|---|---|---|
| 8a[a] | H | 6-Me-benzoxazol-2-yl | 1.17 | 312.1 | $^1$H NMR (400 MHz, DMSO-$d_6$) δ ppm 10.09 (1 H, br. s.), 9.05 (1 H, br. s.), 8.63 (1 H, br. s.), 7.23-7.34 (2 H, m), 7.09 (1 H, d, J = 7.8 Hz), 3.91 (1 H, d, J = 10.5 Hz), 3.79 (1 H, d, J = 10.8 Hz), 3.64 (1 H, d, J = 13.8 Hz), 3.42 (1 H, d, J = 13.8 Hz), 3.17-3.35 (4 H, m), 2.34-2.43 (3 H, m), 2.09-2.23 (2 H, m), 1.79-2.01 (3 H, m). |
| 8b[a] | H | 5-Me-benzoxazol-2-yl | 1.17 | 312.1 | $^1$H NMR (400 MHz, DMSO-$d_6$) δ ppm 10.09 (1 H, br. s.), 9.05 (1 H, br. s.), 8.63 (1 H, br. s.), 7.23-7.34 (2 H, m), 7.09 (1 H, d, J = 7.8 Hz), 3.91 (1 H, d, J = 10.5 Hz), 3.79 (1 H, d, J = 10.8 Hz), 3.64 (1 H, d, J = 13.8 Hz), 3.42 (1 H, d, J = 13.8 Hz), 3.17-3.35 (4 H, m), 2.34-2.43 (3 H, m), 2.09-2.23 (2 H, m), 1.79-2.01 (3 H, m). |
| 53[b,c] | H | 7-Cl-benzothiazol-2-yl | 1.75 | 348.04 | $^1$H NMR (400 MHz, Acetone) δ ppm 12.05 (2 H, br. s.), 11.68 (1 H, br. s.), 9.51 (1 H, br. s.), 7.96 (1 H, dd, J = 8.0, 1.0 Hz), 7.57 (1 H, dd, J = 8.0, 1.0 Hz), 7.40 (1 H, app. t, J = 8.0 Hz), 4.47 (1 H, d, J = 11.0 Hz), 4.27 (1 H, d, J = 11.0 Hz), 3.83-4.00 (2 H, m), 3.60-3.73 (1 H, m), 3.42-3.60 (3 H, m), 2.61-2.67 (1 H, m), 2.38-2.51 (1 H, m), 2.15-2.35 (3 H, m) |
| 54[b] | H | 6-OMe-benzothiazol-2-yl | 1.03 | 344.20 | $^1$H NMR (400 MHz, Acetone) δ ppm 12.80-13.55 (1H, m), 11.73 (1 H, br. s.), 9.73 (1 H, br. s.), 7.85 (1 H, d, J = 8.8 Hz), 7.30 (1 H, d, J = 2.5 Hz), 7.04 (1 H, dd, J = 8.8, 2.5 Hz), 4.43 (1 H, d, J = 11.0 Hz), 4.25 (1 H, d, J = 11.0 Hz), 3.78-3.91 (5 H, m), 3.52-3.64 (1 H, m), 3.37-3.51 (3 H, m), 2.58-2.63 (1 H, m), 2.37-2.49 (1 H, m), 2.14-2.33 (3 H, m) |
| 55[c] | H | 7-F-benzothiazol-2-yl | 1.33 | 331.88 | $^1$H NMR (400 MHz, Acetone) δ ppm 11.84 (1 H, br. s.), 10.04 (2 H, br. s.), 9.56 (1 H, br. s.), 7.82 (1 H, d, J = 8.0 Hz), 7.42 (1 H, td, J = 8.1, 4.6 Hz), 7.30 (1 H, dd, J = 10.8, 8.3 Hz), 4.47 (1 H, d, J = 11.3 Hz), 4.28 (1 H, d, J = 11.3 Hz), 3.86-4.01 (2 H, m), 3.61-3.73 (1 H, m), 3.45-3.61 (3 H, m), 2.60-2.68 (1 H, m), 2.37-2.50 (1 H, m), 2.15- 2.36 (3 H, m) |

TABLE 7-continued

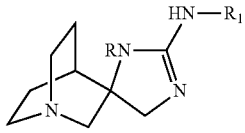

| Example Number | R | R₁ | LCMS RT (min) | LCMS Ion [M + H]⁺ | ¹H NMR |
|---|---|---|---|---|---|
| 56 | H | 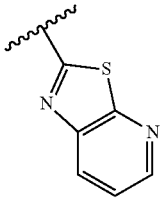 [SMILES: *c1nc2cccnc2s1] | 0.77 | 315.17 | ¹H NMR (400 MHz, Acetone) δ ppm 11.83 (1 H, br. s.), 9.74 (1 H, br. s.), 9.46 (2 H, br. s.), 8.49 (1 H, dd, J = 4.6, 1.4 Hz), 8.07 (1 H, dd, J = 8.3, 1.5 Hz), 7.54 (1 H, dd, J = 8.3, 4.8 Hz), 4.45 (1 H, d, J = 11.0 Hz), 4.27 (1 H, d, J = 11.3 Hz), 3.85-4.00 (2 H, m), 3.60-3.72 (1 H, m), 3.44-3.59 (3 H, m), 2.60-2.68 (1 H, m), 2.38-2.52 (1 H, m), 2.15-2.34 (3 H, m) |
| 57[c] | H | 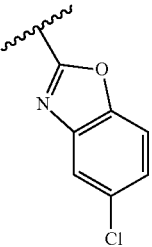 [SMILES: *c1nc2cc(Cl)ccc2o1] | 1.26 | 332.15 | ¹H NMR (400 MHz, Acetone) δ ppm 11.37 (1 H, br. s.), 10.33 (2 H, br. s.), 9.18 (1 H, br. s.), 7.60 (1 H, d, J = 8.8 Hz), 7.49 (1 H, d, J = 2.0 Hz), 7.32 (1 H, dd, J = 8.7, 2.1 Hz), 4.41 (1 H, d, J = 11.3 Hz), 4.23 (1 H, d, J = 11.0 Hz), 3.85-3.97 (2 H, m), 3.60-3.72 (1 H, m), 3.44-3.60 (3 H, m), 2.55-2.63 (1 H, m), 2.38-2.52 (1 H, m), 2.14-2.38 (3 H, m) |
| 58[d] | Me | 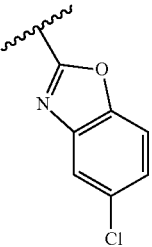 [SMILES: *c1nc2cc(Cl)ccc2o1] | 1.66 | 346.09 | ¹H NMR (400 MHz, Acetone) δ ppm 8.56 (1 H, br. s.), 7.30-7.36 (2 H, m), 7.11 (1 H, dd, J = 8.4, 2.1 Hz), 4.16 (1 H, d, J = 10.3 Hz), 3.97 (1 H, d, J = 10.0 Hz), 3.82-3.90 (1 H, m), 3.65-3.78 (2 H, m), 3.47-3.63 (3 H, m), 3.32 (3 H, s), 2.53-2.63 (2 H, m), 2.29-2.42 (1 H, m), 2.09-2.27 (2 H, m) |
| 59 | H | 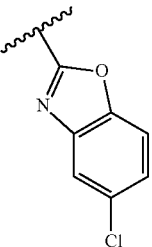 | 2.03 | 298.08 | ¹H NMR (400 MHz, DMSO-d₆) δ ppm 9.77 (1 H, br. s.), 8.66 (1 H, br. s.), 8.36 (1 H, br. s.), 7.41 (1 H, d, J = 7.8 Hz), 7.36 (1 H, d, J = 7.5 Hz), 7.15-7.22 (1 H, m), 7.05-7.15 (1 H, m), 3.82-3.90 (1 H, m), 3.74 (1 H, d, J = 10.3 Hz), 3.62 (1 H, d, J = 13.8 Hz), 3.39 (1 H, d, J = 13.8 Hz), 3.16-3.35 (4 H, m), 2.10-2.21 (2 H, m), 1.80-1.99 (3 H, m) |
| 60 | Me | 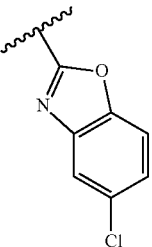 | 0.80 | 312.28 | ¹H NMR (400 MHz, Acetone) δ ppm 12.23 (1 H, br. s.), 8.62 (1 H, br. s.), 7.44-7.53 (2 H, m), 7.37 (1 H, td, J = 7.7, 1.4 Hz), 7.27-7.34 (1 H, m), 4.29 (1 H, d, J = 10.8 Hz), 4.10 (1 H, d, J = 10.5 Hz), 3.96 (1 H, d, J = 1.3 Hz), 3.70-3.87 (2 H, m), 3.51-3.69 (3 H, m), 3.41 (3 H, s), 2.52-2.70 (2 H, m), 2.32-2.45 (1 H, m), 2.12-2.31 (2H, m) |

[a] Following HPLC purification, the free amine was isolated using an MCX cartridge with 2.0 M ammonia in methanol.
[b] The reaction was stirred at ambient temperature for 2 h.
[c] The bis-TFA salt was isolated.
[d] The free base was isolated after silica gel column chromatography.

EXAMPLE 19

N-(5-Methoxy[1,3]thiazolo[5,4-d]pyrimidin-2-yl)-1',5'-dihydrospiro[4-azabicyclo[2.2.2]octane-2,4'-imidazol]-2'-amine

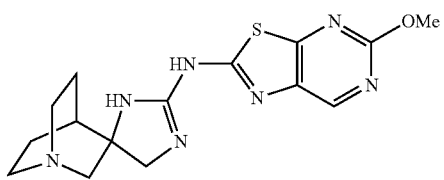 [SMILES: COc1ncc2nc(NC3=NCC4(CN5CCC4CC5)N3)sc2n1]

Step A:
5-Methoxythiazolo[5,4-d]pyrimidin-2-amine

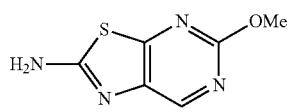

Ethyl 5-chlorothiazolo[5,4-d]pyrimidin-2-ylcarbamate (250 mg, 0.966 mmol) was suspended in MeOH (10 mL) and a 25% (w/w) solution of sodium methoxide in methanol was added (10.0 mL, 46.3 mmol). The resulting solution was refluxed overnight, cooled to ambient temperature, poured into an equal volume of water and extracted with chloroform (4×). A significant amount of compound was still present in the aqueous phase, so this was concentrated to residue, and then dissolved in a small amount of 1N HCl (not enough to make the resulting solution acidic) and extracted again with ethyl acetate (5×). The combined organics were washed with brine, dried over sodium sulfate, filtered, and concentrated in vacuo. 5-Methoxythiazolo[5,4-d]pyrimidin-2-amine (144 mg, 0.790 mmol, 82% yield) was thus obtained as a white solid. $^1$H NMR (400 MHz, DMSO-$d_6$) δ ppm 8.43 (s, 1H) 7.81 (s, 2H) 3.90 (s, 3H). MS (LC/MS) R.T.=0.73; [M+H]$^+$= 183.03.

Step B: Dimethyl 5-methoxythiazolo[5,4-d]pyrimidin-2-ylcarbonimidodithioate

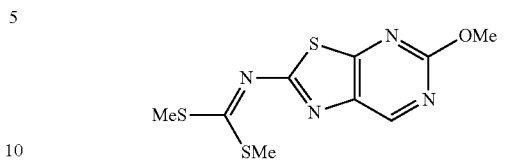

Dimethyl 5-methoxythiazolo[5,4-d]pyrimidin-2-ylcarbonimidodithioate (380 mg, 1.33 mmol, 27% yield) was synthesized according to example 8, step B. $^1$H NMR (400 MHz, CDCl$_3$) δ ppm 8.90 (s, 1H) 4.09 (s, 3H) 2.66 (s, 6H).

Step C: N-(5-Methoxy[1,3]thiazolo[5,4-d]pyrimidin-2-yl)-1',5'-dihydrospiro[4-azabicyclo[2.2.2]octane-2,4'-imidazol]-2'-amine

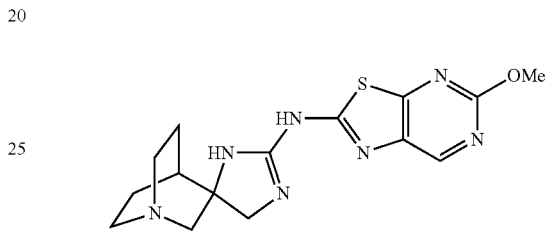

To 3-(aminomethyl)quinuclidin-3-amine (0.048 g, 0.31 mmol) in N,N-dimethylformamide (1.0 mL) was added dimethyl 5-methoxythiazolo[5,4-d]pyrimidin-2-ylcarbonimidodithioate (0.088 g, 0.31 mmol). The suspension was placed into a preheated oil-bath and stirred at 80° C. for 2 h. The reaction flask was removed from the oil-bath and allowed to cool to ambient temperature. The mixture was concentrated and purified by silica gel chromatography (0-30% 9:1 methanol:ammonium hydroxide-chloroform). The product fractions were combined and concentrated in vacuo to afford N-(5-Methoxy[1,3]thiazolo[5,4-d]pyrimidin-2-yl)-1',5'-dihydrospiro[4-azabicyclo[2.2.2]octane-2,4'-imidazol]-2'-amine (14 mg, 0.041 mmol, 13% yield) as a yellow solid. $^1$H NMR (400 MHz, MeOD) δ ppm 8.49 (1H, s), 4.00 (3H, s), 3.92 (1H, d, J=10.0 Hz), 3.59 (1H, d, J=10.0 Hz), 3.35 (1H, d, J=10.0 Hz), 3.04-3.18 (2H, m), 2.74-3.04 (5H, m), 1.91-2.07 (2H, m), 1.60-1.91 (3H, m). MS (LC/MS) R.T.=0.62; [M+H]$^+$=346.18.

The compounds in Table 8 were synthesized according to the method of Example 19 using the appropriate commercially available amine.

TABLE 8

| Example Number | R | R$_1$ | LCMS RT (min) | LCMS Ion [M + H]$^+$ | $^1$H NMR |
|---|---|---|---|---|---|
| 20$^a$ | H | ![pyrimidine-OMe substituent] | 0.54 | 289.90 | $^1$H NMR (400 MHz, MeOD) δ ppm 8.59 (1 H, s), 6.47 (1 H, s), 4.19 (1 H, d, J = 11.0 Hz), 4.01 (3 H, s), 3.95 (1 H, d, J = 11.0 Hz), 3.67-3.73 (2 H, m), 3.45-3.56 (2 H, m), |

TABLE 8-continued

[Structure: quinuclidine-fused imidazoline with RN and HN-R₁ substituents]

| Example Number | R | R₁ | LCMS RT (min) | LCMS Ion [M + H]⁺ | ¹H NMR |
|---|---|---|---|---|---|
| 21 | Me | 6-methoxypyrimidin-4-yl | 0.27 | 303.26 | 3.33-3.45 (2 H, m), 2.37-2.43 (1 H, m), 2.24-2.37 (1 H, m), 2.02-2.16 (3 H, m) ¹H NMR (400 MHz, DMSO-d₆) δ ppm 8.54 (1 H, br. s.), 8.31 (1 H, d, J = 1.0 Hz), 5.97 (1 H, d, J = 1.0 Hz), 3.83 (3 H, s), 3.71 (1 H, d, J = 8.8 Hz), 3.40 (1 H, d, J = 9.3 Hz), 3.09 (3 H, s), 2.98-3.04 (1 H, m), 2.83-2.94 (1 H, m), 2.75-2.83 (2 H, m), 2.66-2.73 (2 H, m), 1.85-2.04 (2 H, m), 1.67-1.83 (1 H, m), 1.40-1.57 (2 H, m) |
| 23 | H | quinazolin-4-yl | 0.55 | 309.23 | ¹H NMR (500 MHz, DMSO-d₆) δ ppm 8.75-8.80 (2 H, m), 8.55 (1 H, s), 8.40 (1 H, d, J = 8.2 Hz), 7.70-7.76 (1 H, m), 7.65 (1 H, d, J = 8.2 Hz), 7.42-7.49 (1 H, m), 3.81 (1 H, d, J = 10.1 Hz), 3.51 (1 H, d, J = 10.1 Hz), 2.94-3.01 (1 H, m), 2.87-2.94 (1 H, m), 2.79-2.87 (1 H, m), 2.61-2.75 (3 H, m), 1.86-1.96 (1 H, m), 1.79-1.85 (1 H, m), 1.60-1.72 (1 H, m), 1.37-1.60 (2 H, m) |
| 24 | Me | quinazolin-4-yl | 0.64 | 323.27 | ¹H NMR (500 MHz, MeOD) δ ppm 8.55-8.61 (2 H, m), 7.74-7.81 (1 H, m), 7.69 (1 H, d, J = 8.2 Hz), 7.49-7.55 (1 H, m), 3.98 (1 H, d, J = 9.8 Hz), 3.64 (1 H, d, J = 10.1 Hz), 3.40 (3 H, s), 3.21-3.28 (1 H, m), 2.82-3.12 (5 H, m), 2.18-2.28 (1 H, m), 2.10-2.14 (1 H, m), 1.92-2.02 (1 H, m), 1.58-1.80 (2 H, m) |
| 28 | H | 6-chlorothiazolo[5,4-b]pyridin-2-yl | 0.79 | 349.16 | ¹H NMR (400 MHz, MeOD) δ ppm 7.78 (1 H, d, J = 8.5 Hz), 7.30 (1 H, d, J = 8.3 Hz), 3.93 (1 H, d, J = 10.3 Hz), 3.58 (1 H, d, J = 10.0 Hz), 3.04-3.15 (2 H, m), 2.72-3.02 (4 H, m), 1.91-2.04 (2 H, m), 1.77-1.88 (1 H, m), 1.64-1.77 (2 H, m) |

TABLE 8-continued

| Example Number | R | R₁ | LCMS RT (min) | LCMS Ion [M + H]⁺ | ¹H NMR |
|---|---|---|---|---|---|
| 28a[b] | H | thiazolo-pyridine-Cl | 0.72 | 349.19 | ¹H NMR (400 MHz, MeOD) δ ppm 7.78 (1 H, d, J = 8.5 Hz), 7.30 (1 H, d, J = 8.3 Hz), 3.93 (1 H, d, J = 10.3 Hz), 3.58 (1 H, d, J = 10.0 Hz), 3.04-3.15 (2 H, m), 2.72-3.02 (4 H, m), 1.91-2.04 (2 H, m), 1.77-1.88 (1 H, m), 1.64-1.77 (2 H, m) |
| 28b[b] | H | thiazolo-pyridine-Cl | 0.73 | 349.19 | ¹H NMR (400 MHz, MeOD) δ ppm 7.78 (1 H, d, J = 8.5 Hz), 7.30 (1 H, d, J = 8.3 Hz), 3.93 (1 H, d, J = 10.3 Hz), 3.58 (1 H, d, J = 10.0 Hz), 3.04-3.15 (2 H, m), 2.72-3.02 (4 H, m), 1.91-2.04 (2 H, m), 1.77-1.88 (1 H, m), 1.64-1.77 (2 H, m) |
| 29 | Me | thiazolo-pyridine-Cl | 0.86 | 363.16 | ¹H NMR (400 MHz, MeOD) δ ppm 7.75 (1 H, d), 7.29 (1 H, d, J = 8.5 Hz), 3.93 (1 H, d, J = 9.8 Hz), 3.57 (1 H, d, J = 9.8 Hz), 3.18-3.25 (4 H, m), 2.76-3.08 (5 H, m), 2.06-2.20 (2 H, m), 1.86-2.00 (1 H, m), 1.59-1.77 (2 H, m) |
| 30[c,d] | H | thiazolo-pyrazine-Br | 2.52 | 396.1 | ¹H NMR (400 MHz, CHLOROFORM-d) δ ppm 8.39 (1 H, s), 3.94 (1 H, d, J = 10.0 Hz), 3.56 (1 H, d, J = 9.8 Hz), 3.06-3.19 (2 H, m), 2.72-3.01 (4 H, m), 2.00-2.07 (1 H, m), 1.78-1.93 (1 H, m), 1.62-1.78 (3 H, m) |
| 31[c] | Me | thiazolo-pyrazine-Br | 2.79 | 250.1 | ¹H NMR (400 MHz, CHLOROFORM-d) δ ppm 8.70 (1 H, br. s.), 8.36 (1 H, s), 3.91 (1 H, d, J = 9.5 Hz), 3.50 (1 H, d, J = 9.5 Hz), 3.15-3.27 (4 H, m), 2.73-3.04 (5 H, m), 1.98-2.13 (2 H, m), 1.76-1.89 (1 H, m), 1.57-1.71 (2 H, m) |
| 38 | H | thiazolo-pyrimidine-OMe | 0.64 | 346.14 | ¹H NMR (400 MHz, MeOD) δ ppm 8.39 (1 H, s), 4.14 (3 H, s), 3.93 (1 H, d, J = 10.0 Hz), 3.59 (1 H, d, J = 10.3 Hz), 3.12-3.16 (1 H, m), 3.07-3.12 (2 H, m), 2.74-2.97 (4 H, m), 1.94-2.02 (1 H, m), 1.64-1.87 (3 H, m) |

TABLE 8-continued

| Example Number | R | R₁ (substituent) | LCMS RT (min) | LCMS Ion [M + H]⁺ | ¹H NMR |
|---|---|---|---|---|---|
| 39[f] | H | thiazolo[5,4-b]pyridine-2-yl with OBn | 1.23 | 421.21 | ¹H NMR (400 MHz, MeOD) δ ppm 7.77 (1 H, d, J = 8.8Hz), 7.45 (2 H, d, J = 7.0 Hz), 7.33-7.40 (2 H, m), 7.25-7.33 (1 H, m), 6.78 (1 H d, J = 8.5 Hz), 5.35 (2 H, s), 3.89 (1 H, d, J = 10.0 Hz), 3.55 (1 H, d, J = 10.0 Hz), 3.03-3.13 (2 H, m), 2.74-3.00 (4 H, m), 1.91-2.03 (2 H, m), 1.65-1.88 (3 H, m) |
| 41[g] | H | thiazolo[5,4-b]pyrazine-2-yl with Me | 0.72 | 330.19 | ¹H NMR (400 MHz, MeOD) δ ppm 8.18 (1 H, s), 3.95 (1 H, d, J = 10.3 Hz), 3.60 (1 H, d, J = 10.3 Hz), 3.05-3.16 (2 H, m), 2.74-3.05 (4 H, m), 2.54 (3 H, s), 1.94-2.08 (2 H, m), 1.64-1.89 (3 H, m) |
| 43 | H | 4,6-dimethyl-1,3,5-triazin-2-yl | 0.17 | 288.21 | ¹H NMR (400 MHz, MeOD) δ ppm 3.92 (1 H, d, J = 10.3 Hz), 3.57 (1 H, d, J = 10.3 Hz), 2.99-3.14 (2 H, m), 2.72-2.97 (4 H, m), 2.37-2.44 (6 H, m), 1.88-2.02 (2 H, m), 1.64-1.86 (3 H, m) |
| 46 | H | thiazolo[5,4-b]pyridine-2-yl with OMe | 0.90 | 345.2 | ¹H NMR (400 MHz, MeOD) δ ppm 7.75 (1 H, d, J = 8.5 Hz), 6.72 (1 H, d, J = 8.5 Hz), 3.92 (3 H, s), 3.89 (1 H, d, J = 10.0 Hz), 3.55 (1 H, d, J = 9.8 Hz), 3.02-3.15 (2 H, m), 2.75-2.99 (4 H, m), 1.91-2.03 (2 H, m), 1.63-1.88 (3 H, m) |
| 47 | Me | thiazolo[5,4-b]pyridine-2-yl with OMe | 0.68 | 359.18 | ¹H NMR (400 MHz, MeOD) δ ppm 7.72 (1 H, d, J = 8.8 Hz), 6.71 (1 H, d, J = 8.8 Hz), 3.86-3.94 (4 H, m), 3.53 (1 H, d, J = 9.8 Hz), 3.15-3.24 (4 H, m), 2.76-3.06 (5 H, m), 2.03-2.20 (2 H, m), 1.85-1.99 (1 H, m), 1.54-1.75 (2 H, m) |
| 52[a] | H | 6-chlorobenzothiazol-2-yl | 1.40 | 348.12 | ¹H NMR (400 MHz, Acetone) δ ppm 13.52 (1 H, br. s.), 11.77 (1 H, br. s.), 9.69 (1 H, br. s.), 8.07 (1 H, d, J = 2.0 Hz), 7.74 (1 H, d, J = 8.5 Hz), 7.50 (1 H, dd, J = 8.7, 2.1 Hz), 4.44 (1 H, d, J = 11.0 Hz), 4.26 (1 H, d, J = 11.3 Hz), 3.81-4.00 (2 H, m), |

TABLE 8-continued

| Example Number | R | R₁ | LCMS RT (min) | LCMS Ion [M + H]⁺ | ¹H NMR |
|---|---|---|---|---|---|
| | | | | | 3.59-3.72 (1 H, m), 3.42-3.58 (3 H, m), 2.59-2.67 (1 H, m), 2.37-2.52 (1 H, m), 2.14-2.37 (3 H, m) |
| 61[h] | H | (pyrimidine-imidazole) | 0.39 | 325.1 | ¹H NMR (400 MHz, MeOD) δ ppm 8.57 (1 H, d, J = 1.0 Hz), 8.54 (1 H, s), 7.85 (1 H, s), 7.15 (1 H, s), 6.80 (1 H, d, J = 1.0 Hz), 3.90 (1 H, d, J = 10.0 Hz), 3.55 (1 H, d, J = 10.0 Hz), 3.02-3.16 (2 H, m), 2.73-3.02 (4 H, m), 1.92-2.04 (2 H, m), 1.64-1.89 (3 H, m) |
| 64[i] | H | (7-methylpyrrolo[2,1-f][1,2,4]triazine) | 1.35 | 312.24 | ¹H NMR (400 MHz, METHANOL-d₄) δ 7.96 (s, 1 H), 6.79 (d, J = 4.3 Hz, 1 H), 6.45 (dd, J = 4.3, 0.5 Hz, 1 H), 3.91 (d, J = 10.3 Hz, 1 H), 3.59-3.52 (m, 1 H), 3.09 (s, 2 H), 3.01-2.71 (m, 4 H), 2.47 (s, 3 H), 2.04-1.90 (m, 2 H), 1.87-1.63 (m, 3 H) |
| 66[i] | H | (7-bromopyrrolo[2,1-f][1,2,4]triazine) | 1.33 | 378.08 | ¹H NMR (500 MHz, METHANOL-d₄) δ 8.06 (s, 1 H), 6.93 (d, J = 4.6 Hz, 1 H), 6.73 (d, J = 4.4 Hz, 1 H), 3.98 (d, J = 10.4 Hz, 1 H), 3.67 (d, J = 10.4 Hz, 1 H), 3.32-3.24 (m, 2 H), 3.19-2.92 (m, 4 H), 2.18-2.06 (m, 2 H), 1.97-1.79 (m, 3 H) |

[a]The final product was purified by reverse phase preparatory HPLC (0-100% TFA-methanol-water) to afford the TFA salt.

[b]The enantiomers were separated using a Chiralpak OJ-H (4.6 × 250 mm, 5 μm) column with a mobile phase consisting of 15% methanol (0.1% DEA) in CO₂. The wavelength was set at 320 nM. The separated peaks were concentrated in vacuo to yield yellow solids.

[c]The amine was synthesized according to Bozidar, K.; et al. *Heterocycles* 1987, 26, 689-697.

[d]The amine protons were washed out with MeOD.

[e]The amine was synthesized according to US 2007270433 (A1).

[f]5-(Benzyloxy)thiazolo[5,4-b]pyridin-2-amine (1.95 g, 7.58 mmol, 47% yield) was prepared according to example 44, step A from 6-(benzyloxy)pyridin-3-amine (prepared according to WO2006/044707). ¹H NMR (400 MHz, CDCl₃) δ ppm 7.70 (d, J = 8.78 Hz, 1 H) 7.48 (d, J = 7.28 Hz, 2 H) 7.39 (t, J = 7.28 Hz, 2 H) 7.30-7.36 (m, 1 H) 6.78 (d, J = 8.78 Hz, 1 H) 5.39 (s, 2 H) 5.14 (br. s., 2 H).

[g]The amine was synthesized according to Bozidar, K.; et al. *Heterocycles* 1987, 26, 689-697. ¹H NMR (500 MHz, DMSO-d6) δ ppm 8.26 (2 H, br. s.), 8.12 (1 H, s), 2.43 (3 H, s). MS (LC/MS) R.T. = 0.66; [M + H]⁺ = 167.0.

[h]The reaction was stirred at 100° C. for 24 h.

[i]The reaction was stirred at 60° C. for 45 min.

EXAMPLE 32

N-[1,3]Thiazolo[4,5-b]pyrazin-2-yl-1',5'-dihydrospiro[4-azabicyclo[2.2.2]octane-2,4'-imidazol]-2'-amine

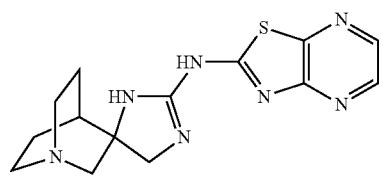 [SMILES: c1cnc2sc(NC3=NCC4(CN5CCC4CC5)N3)nc2n1]

A nitrogen-filled, round-bottomed flask was charged with N-(6-bromo[1,3]thiazolo[4,5-b]pyrazin-2-yl)-1',5'-dihydrospiro[4-azabicyclo[2.2.2]octane-2,4'-imidazol]-2'-amine (25 mg, 0.063 mmol, example 30) and palladium on carbon (10% by weight, 34 mg, 0.032 mmol). Methanol (25 mL) was slowly added to the dry reaction mixture. The reaction flask was evacuated, fitted with a hydrogen gas balloon, and stirred at ambient temperature for 18 h. The hydrogen gas was removed under reduced pressure and the flask was back-filled with nitrogen gas. The crude reaction mixture was filtered through Celite® and the filtrate was concentrated and purified by silica gel chromatography (0-30% 9:1 methanol ammonium hydroxide-chloroform). The product fractions were combined and concentrated in vacuo to afford N-[1,3]thiazolo[4,5-b]pyrazin-2-yl-1',5'-dihydrospiro[4-azabicyclo[2.2.2]octane-2,4'-imidazol]-2'-amine (16 mg, 0.049 mmol, 78% yield) as a yellow solid. $^1$H NMR (400 MHz, MeOD) δ ppm 8.27 (1H, d, J=3.0 Hz), 8.14 (1H, d, J=3.0 Hz), 3.96 (1H, d, J=10.3 Hz), 3.62 (1H, d, J=10.3 Hz), 3.05-3.17 (2H, m), 2.73-3.04 (4H, m), 1.95-2.08 (2H, m), 1.62-1.89 (3H, m). MS (LC/MS) R.T.=0.57; [M+H]$^+$=316.16.

EXAMPLE 33

3'-Methyl-N-[1,3]thiazolo[4,5-b]pyrazin-2-yl-3',5'-dihydrospiro[4-azabicyclo[2.2.2]octane-2,4'-imidazol]-2'-amine

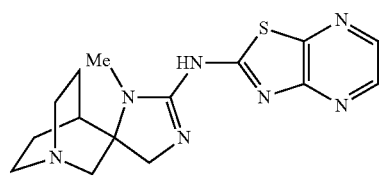 [SMILES: CN1C(Nc2nc3nccnc3s2)=NCC12CN1CCC2CC1]

Prepared in 75% yield from N-(6-bromo[1,3]thiazolo[4,5-b]pyrazin-2-yl)-3'-methyl-3',5'-dihydrospiro[4-azabicyclo[2.2.2]octane-2,4'-imidazol]-2'-amine (example 31) according to the procedure for example 32. $^1$H NMR (400 MHz, DMSO-d$_6$) δ ppm 8.47 (1H, br. s.), 8.34 (1H, d, J=2.8 Hz), 8.17 (1H, d, J=2.8 Hz), 3.88 (1H, d, J=10.3 Hz), 3.56 (1H, d, J=10.3 Hz), 3.15 (3H, s), 3.08 (1H, d, J=14.8 Hz), 2.75-2.95 (3H, m), 2.67-2.75 (2H, m), 1.91-2.03 (2H, m), 1.69-1.83 (1H, m), 1.40-1.61 (2H, m). MS (LC/MS) R.T.=0.77; [M+H]$^+$=330.19.

EXAMPLE 42

2-(1',5'-Dihydrospiro[4-azabicyclo[2.2.2]octane-2,4'-imidazol]-2'-ylamino)[1,3]thiazolo[5,4-b]pyridin-5(4H)-one

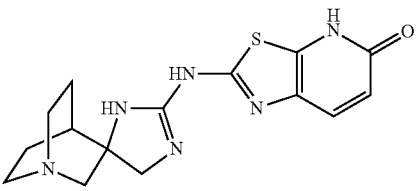 [SMILES: O=c1ccc2nc(NC3=NCC4(CN5CCC4CC5)N3)sc2[nH]1]

A round-bottomed flask was charged with N-(5-(benzyloxy)[1,3]thiazolo[5,4-b]pyridin-2-yl)-1',5'-dihydrospiro[4-azabicyclo[2.2.2]octane-2,4'-imidazol]-2'-amine (75 mg, 0.18 mmol, example 39). Trifluoroacetic acid (1.8 mL) was subsequently added to the reaction flask and the reaction mixture was stirred at ambient temperature for 18 h. The volatiles were then removed under reduced pressure, and the crude material was dissolved in methanol and loaded onto an MCX cartridge and washed with methanol (10 mL). The material was then flushed from the cartridge with ammonia (2M) in methanol (10 mL). The volatiles were removed under reduced pressure and the crude material was purified by silica gel chromatography (0-30% 9:1 methanol:ammonium hydroxide-chloroform). The product fractions were combined and concentrated in vacuo to afford 2-(1',5'-dihydrospiro[4-azabicyclo[2.2.2]octane-2,4'-imidazol]-2'-ylamino)[1,3]thiazolo[5,4-b]pyridin-5 (4H)-one (64 mg, 0.14 mmol, 80% yield) as a white solid. $^1$H NMR (400 MHz, DMSO-d$_6$) δ ppm 9.79 (1H, br. s.), 8.78 (1H, br. s.), 8.53 (1H, br. s.), 7.76 (1H, d, J=8.8 Hz), 6.64 (1H, d, J=8.5 Hz), 3.87 (1H, d, J=10.5 Hz), 3.74 (1H, d, J=10.5 Hz), 3.62 (1H, d, J=13.8 Hz), 3.41 (1H, d, J=13.6 Hz), 3.14-3.36 (4H, m), 2.04-2.24 (2H, m), 1.77-1.98 (3H, m). MS (LC/MS) R.T.=0.25; [M+H]$^+$=331.20.

EXAMPLE 44

N-(5-Fluoro[1,3]thiazolo[5,4-b]pyridin-2-yl)-1',5'-dihydrospiro[4-azabicyclo[2.2.2]octane-2,4'-imidazol]-2'-amine

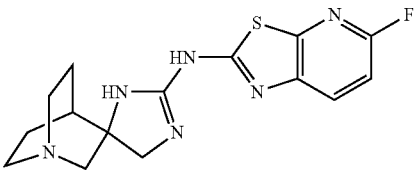 [SMILES: Fc1ccc2nc(NC3=NCC4(CN5CCC4CC5)N3)sc2n1]

Step A: 5-Fluorothiazolo[5,4-b]pyridin-2-amine

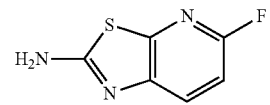 [SMILES: Nc1nc2ccc(F)nc2s1]

A three-neck flask was fitted with a mechanical stirrer and charged with potassium rhodanate (25.1 g, 258 mmol) and acetic acid (81 mL). The suspension was stirred at 0° C. while 6-methoxypyridin-3-amine (4.00 g, 32.2 mmol) was added. A solution of bromine (5.15 mL, 100 mmol) in acetic acid (27 mL) was added over 30 min via an addition funnel. After bromine addition was complete, the ice-water bath was removed and the reaction mixture was allowed to warm to ambient temperature and was stirred at that temperature for 16 h. Water (30 mL) was added to the reaction mixture and it was placed into a preheated oil-bath and stirred at 85° C. for 20 min. The solids were filtered hot, collected, and recrystallized from methanol to afford 5-fluorothiazolo[5,4-b]pyridin-2-amine (2.38 g, 13.1 mmol, 41% yield) as a yellow solid. $^1$H NMR (400 MHz, CHLOROFORM-d) δ ppm 7.68 (1H, d, J=8.5 Hz), 6.71 (1H, d, J=8.5 Hz), 5.11 (2H, br. s.), 3.95 (3H, s). MS (LC/MS) R.T.=0.63; [M+H]$^+$=182.08.

Step B: Dimethyl 5-fluorothiazolo[5,4-b]pyridin-2-ylcarbonimidodithioate

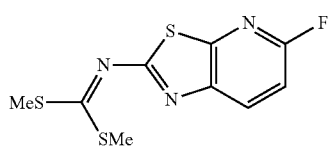 [SMILES: CSC(=Nc1nc2ccc(F)nc2s1)SC]

Dimethyl 5-fluorothiazolo[5,4-b]pyridin-2-ylcarbonimidodithioate (2.17 g, 7.94 mmol, 67% yield) was synthesized according to example 8, step B. $^1$H NMR (500 MHz, CHLOROFORM-d) δ ppm 8.14 (1H, dd, J=8.5, 7.0 Hz), 6.98 (1H, dd, J=8.7, 2.0 Hz), 2.63 (6H, s). MS (LC/MS) R.T.=1.86; [M+H]$^+$=274.1.

Step C: N-(5-Fluoro[1,3]thiazolo[5,4-b]pyridin-2-yl)-1',5'-dihydrospiro[4-azabicyclo[2.2.2]octane-2,4'-imidazol]-2'-amine

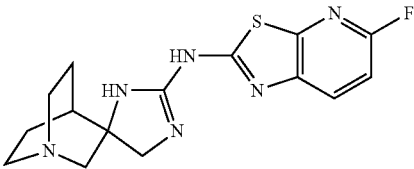 [SMILES: Fc1ccc2nc(NC3=NCC4(CN5CCC4CC5)N3)sc2n1]

N-(5-Fluoro[1,3]thiazolo[5,4-b]pyridin-2-yl)-1',5'-dihydrospiro[4-azabicyclo[2.2.2]octane-2,4'-imidazol]-2'-amine (235 mg, 0.698 mmol, 99% yield) was synthesized according to example 8, step C. $^1$H NMR (400 MHz, MeOD) δ ppm 7.91 (1H, dd), 6.95 (1H, dd, J=8.8, 1.5 Hz), 3.92 (1H, d, J=10.3 Hz), 3.57 (1H, d, J=10.0 Hz), 3.02-3.16 (2H, m), 2.73-3.01 (4H, m), 1.91-2.03 (2H, m), 1.77-1.89 (1H, m), 1.63-1.77 (2H, m). MS (LC/MS) R.T.=0.51; [M+H]$^+$=333.18.

The compounds in Table 9 were synthesized according to the method of Example 44 using the appropriate amine.

TABLE 9

| Example Number | R | R$_1$ | LCMS RT (min) | LCMS Ion [M + H]$^+$ | $^1$H NMR |
|---|---|---|---|---|---|
| 45 | Me | thiazolo[5,4-b]pyridine-F | 0.63 | 347.23 | $^1$H NMR (400 MHz, MeOD) δ ppm 7.89 (1 H, dd, J = 8.5, 7.0 Hz), 6.94 (1 H, dd, J = 8.5, 1.5 Hz), 3.93 (1 H, d, J = 9.8 Hz), 3.56 (1 H, d, J = 10.0 Hz), 3.19 (3 H, s), 2.89-3.08 (3 H, m), 2.76-2.89 (2 H, m), 2.06-2.20 (2 H, m), 1.86-1.99 (1 H, m), 1.57-1.76 (2 H, m) |
| 49$^a$ | H | thiazolo[5,4-b]pyridine-Br | 0.81 | 395.14 | $^1$H NMR (400 MHz, DMSO-d$_6$) δ ppm 8.51 (1H, br. s), 8.19 (1 H, br. s), 7.68 (1 H, d, J = 8.3 Hz), 7.48 (1 H, d, J = 8.3 Hz), 3.80 (1 H, d, J = 10.0 Hz), 3.51 (1 H, d, J = 10.0 Hz), 2.96 (1 H, d, J = 1.3 Hz), 2.61-2.91 (5 H, m), 1.79-1.93 (2 H, m), 1.59-1.70 (1 H, m), 1.39-1.57 (2 H, m) |

TABLE 9-continued

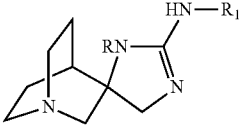

| Example Number | R | R₁ | LCMS RT (min) | LCMS Ion [M + H]⁺ | ¹H NMR |
|---|---|---|---|---|---|
| 50[a] | Me | (thiazolo[5,4-b]pyridine with Br) | 1.04 | 409.2 | ¹H NMR (500 MHz, DMSO-d₆) δ ppm 8.40 (1 H, br. s.), 7.69 (1 H, d, J = 8.5 Hz), 7.50 (1 H, d, J = 8.5 Hz), 3.81 (1 H, d, J = 9.8 Hz), 3.49 (1 H, d, J = 10.1 Hz), 3.09 (3 H, s), 3.04 (1 H, d, J = 14.6 Hz), 2.73-2.93 (3 H, m), 2.65-2.72 (2 H, m), 1.89-2.00 (2 H, m), 1.67-1.80 (1 H, m), 1.39-1.55 (2 H, m) |

[a]5-Bromothiazolo[5,4-b]pyridin-2-amine (2.73 g, 11.9 mmol, 51% yield) was synthesized according to example 44, step A.
¹H NMR (400 MHz, DMSO-d₆) δ ppm 7.94 (2 H, br. s.), 7.58 (1 H, d, J = 8.3 Hz), 7.44 (1 H, d, J = 8.5 Hz). MS (LC/MS) R.T. = 0.87; [M + H]⁺ = 231.97.

EXAMPLE 48

N~2~-(1',5'-Dihydrospiro[4-azabicyclo[2.2.2]octane-2,4'-imidazol]-2'-yl)-N~5~,N~5~-dimethyl[1,3]thiazolo[5,4-b]pyridine-2,5-diamine

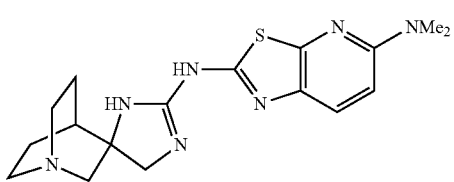 [SMILES: CN(C)c1ccc2nc(NC3=NCC4(CN5CCC4CC5)N3)sc2n1]

A round-bottomed flask was charged with N-(5-fluoro[1,3]thiazolo[5,4-b]pyridin-2-yl)-1',5'-dihydrospiro[4-azabicyclo[2.2.2]octane-2,4'-imidazol]-2'-amine (30 mg, 0.090 mmol, example 44) and dimethylamine in methanol (0.2 M, 4.5 mL, 0.90 mmol). The reaction mixture was stirred at 60° C. for 72 h. The volatiles were removed under reduced pressure and the crude product was purified by reverse phase preparatory HPLC (0-100% TFA-methanol-water). The product fractions were combined and concentrated in vacuo to afford N~2~-(1',5'-dihydrospiro[4-azabicyclo[2.2.2]octane-2,4'-imidazol]-2'-yl)-N~5~-N~5~-dimethyl[1,3]thiazolo[5,4-b]pyridine-2,5-diamine as the trifluoroacetic acid salt (11 mg, 0.022 mmol, 25% yield) as a yellow oil. ¹H NMR (400 MHz, MeOD) δ ppm 7.85 (1H, d, J=9.3 Hz), 6.80 (1H, d, J=9.3 Hz), 4.20 (1H, d, J=11.0 Hz), 3.97 (1H, d, J=11.0 Hz), 3.66-3.80 (2H, m), 3.33-3.54 (4H, m), 3.14 (6H, s), 2.22-2.46 (3H, m), 2.04-2.18 (2H, m). MS (LC/MS) R.T.=0.77; [M+H]⁺=358.27.

EXAMPLE 62

N-(3,5-Dihydro-1'-azaspiro[imidazole-4,3'-bicyclo[2.2.2]octane]-2-yl)-5-methyloxazolo[5,4-b]pyridin-2-amine

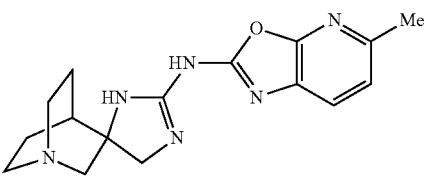 [SMILES: Cc1ccc2nc(NC3=NCC4(CN5CCC4CC5)N3)oc2n1]

Step A: 5-Methyloxazolo[5,4-b]pyridin-2-amine

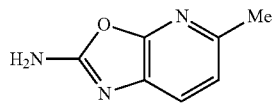

A round-bottomed flask was charged with 3-amino-6-methylpyridin-2 (1H)-one (3.91 g, 31.5 mmol) and di(1H-imidazol-1-yl)methanimine (7.62 g, 47.3 mmol). THF (63.0 mL) was added to the reaction flask at ambient temperature. The flask was then placed into a preheated oil-bath at 65° C. and stirred at that temperature. After 16 h, the reaction vessel was removed from the oil-bath and allowed to cool to ambient temperature. The volatiles were removed to ⅓ original volume under reduced pressure before the solids were filtered and washed with THF (100 mL) to afford 5-methyloxazolo[5,4-b]pyridin-2-amine (3.17 g, 21.2 mmol, 67% yield) as a tan solid. MS (LC/MS) R.T.=0.88; [M+H]⁺=150.27.

69

Step B: N-(3,5-Dihydro-1'-azaspiro[imidazole-4,3'-bicyclo[2.2.2]octane]-2-yl)-5-methyloxazolo[5,4-b]pyridin-2-amine

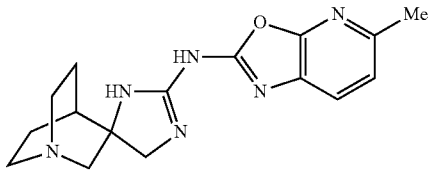 [SMILES: Cc1ccc2nc(NC3=NCC4(CN5CCC4CC5)N3)oc2n1]

A round-bottomed flask was charged with 5-methyloxazolo[5,4-b]pyridin-2-amine (150 mg, 1.01 mmol) and NaH (44.2 mg, 1.11 mmol). DMF (5.0 mL) was slowly added at ambient temperature and the reaction was stirred. After 15 min, 1,1'-thiocarbonyldipyridin-2 (1H)-one (257 mg, 1.11 mmol) was added to the reaction mixture and it was stirred at ambient temperature. After 1 h, LC/MS showed complete conversion to the isothiocyanate and 3-(aminomethyl)quinuclidin-3-amine (221 mg, 1.31 mmol) and $Cs_2CO_3$ (655 mg, 2.01 mmol) were added to the isothiocyanate solution. The reaction mixture was heated to 150° C. for 20 min in a microwave reactor. LC/MS showed complete conversion to the desired product. The reaction was diluted with water and extracted with chloroform (3×75 mL). The combined organic layers were dried over sodium sulfate and the volatiles removed under reduced pressure. The crude material was loaded onto a biotage silica gel column and purified using ammonium hydroxide in methanol (10%) and chloroform (0-7%) to afford N-((3'R,4'S)-3,5-dihydro-1'-azaspiro[imidazole-4,3'-bicyclo[2.2.2]octane]-2-yl)-5-methyloxazolo[5,4-b]pyridin-2-amine (7.8 mg, 0.025 mmol, 2.5% yield) as a white solid. $^1$H NMR (400 MHz, MeOD) δ ppm 7.58 (1H, d, J=7.8 Hz), 7.08 (1H, d, J=7.8 Hz), 3.90-3.96 (1H, m), 3.56-3.62 (1H, m), 3.03-3.17 (2H, m), 2.73-3.03 (4H, m), 2.51 (3H, s), 1.93-2.05 (2H, m), 1.63-1.88 (3H, m). MS (LC/MS) R.T.=1.18; [M+H]$^+$=313.17.

EXAMPLE 63

N-(3,5-dihydro-1'-azaspiro[imidazole-4,3'-bicyclo[2.2.2]octane]-2-yl)-6-methylbenzo[d]thiazol-2-amine

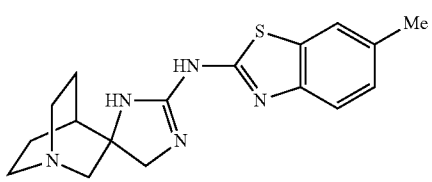 [SMILES: Cc1ccc2nc(NC3=NCC4(CN5CCC4CC5)N3)sc2c1]

N-(3,5-dihydro-1'-azaspiro[imidazole-4,3'-bicyclo[2.2.2]octane]-2-yl)-6-methylbenzo[d]thiazol-2-amine (35 mg, 0.10 mmol, 11% yield) was synthesized according to example 62, step B. $^1$H NMR (400 MHz, MeOD) δ ppm 7.41-7.46 (2H, m), 7.08-7.13 (1H, m), 3.88 (1H, d, J=10.0 Hz), 3.54 (1H, d, J=10.0 Hz), 3.03-3.16 (2H, m), 2.71-3.02 (4H, m), 2.39 (3H, s), 1.91-2.05 (2H, m), 1.64-1.88 (3H, m). MS (LC/MS) R.T.=1.41; [M+H]$^+$=328.1.

70

EXAMPLE 65

N-(7-Chloropyrrolo[1,2-f][1,2,4]triazin-4-yl)-3,5-dihydro-1'-azaspiro[imidazole-4,3'-bicyclo[2.2.2]octan]-2-amine

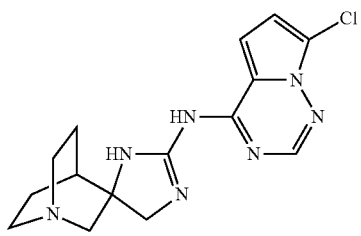 [SMILES: Clc1ccc2c(NC3=NCC4(CN5CCC4CC5)N3)ncnn12]

Step A:
7-Chloropyrrolo[1,2-f][1,2,4]triazin-4-amine

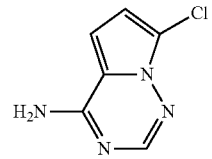 [SMILES: Nc1ncnn2c(Cl)ccc12]

To a brown solution of pyrrolo[2,1-f][1,2,4]triazin-4-amine (1.35 g, 10.1 mmol) in DMF (20 mL) was added N-chlorosuccinimide (1.34 g, 10.1 mmol) at ambient temperature under an inert atmosphere of nitrogen gas. The brown reaction mixture was stirred for 72 h. LC/MS showed approximately 80% conversion to the desired product. The reaction mixture was partitioned between brine and EtOAc (50 mL/200 mL) and separated. The organic phase was washed with brine (50 mL), dried over $MgSO_4$, and the volatiles were removed under reduced pressure. The resulting residue was dissolved in a minimum amount of DMF, and purified by silica gel chromatography with EtOAc in Hexanes (0-50%) to afford two major peaks. The volatiles were removed under reduced pressure before the white solid was dissolved in MeOH (10 mL) and TFA (1 mL) and purified on reverse phase chromatography eluting with a water/TFA/methanol mixture. The collected fractions were neutralized by passing them through a UCT CHQAX15M25 cartridge to afford 7-chloropyrrolo[2,1-f][1,2,4]triazin-4-amine (388 mg, 2.30 mmol, 23% yield) as an off-white powder. $^1$H NMR (400 MHz, DMSO-d$_6$) δ 8.87-8.25 (m, 2H), 8.07 (s, 1H), 7.20 (d, J=4.8 Hz, 1H), 6.83 (d, J=4.8 Hz, 1H). MS (LC/MS) R.T.=1.24; [M+H]$^+$=169.1.

Step B: Dimethyl 7-chloropyrrolo[1,2-f][1,2,4]triazin-4-ylcarbonimidodithioate

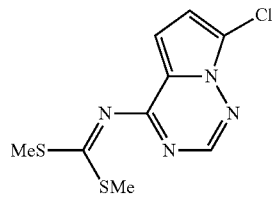 [SMILES: CSC(=Nc1ncnn2c(Cl)ccc12)SC]

Dimethyl 7-chloropyrrolo[1,2-f][1,2,4]triazin-4-ylcarbonimidodithioate (940 mg, 3.45 mmol, 61% yield) was synthesized according to example 8, step B. $^1$H NMR (400 MHz, DMSO-$d_6$) δ 8.48 (s, 1H), 7.08-7.05 (m, 1H), 7.04-7.03 (m, 1H), 2.65 (s, 6H).

Step C: N-(7-Chloropyrrolo[1,2-f][1,2,4]triazin-4-yl)-3,5-dihydro-1'-azaspiro[imidazole-4,3'-bicyclo[2.2.2]octan]-2-amine

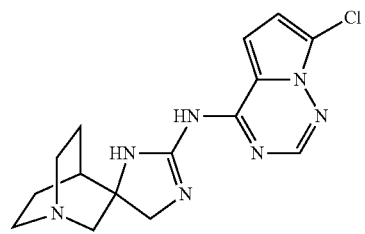 [SMILES: Clc1ccc2c(NC3=NCC4(CN5CCC4CC5)N3)ncnn12]

N-(7-Chloropyrrolo[1,2-f][1,2,4]triazin-4-yl)-3,5-dihydro-1'-azaspiro[imidazole-4,3'-bicyclo[2.2.2]octan]-2-amine (13 mg, 0.039 mmol, 4% yield) was synthesized according to example 64. $^1$H NMR (500 MHz, METHANOL-$d_4$) δ 8.05 (s, 1H), 6.89 (d, J=4.6 Hz, 1H), 6.64 (d, J=4.6 Hz, 1H), 3.98 (d, J=10.4 Hz, 1H), 3.66 (d, J=10.2 Hz, 1H), 3.31-3.20 (m, 2H), 3.13-2.91 (m, 4H), 2.14-2.04 (m, J=3.1, 3.1 Hz, 2H), 1.95-1.77 (m, 3H). MS (LC/MS) R.T.=1.26; [M+H]$^+$=332.2.

EXAMPLE 67

N-(6-Methoxybenzo[d]thiazol-2-yl)-5H-1'-azaspiro[oxazole-4,3'-bicyclo[2.2.2]octan]-2-amine

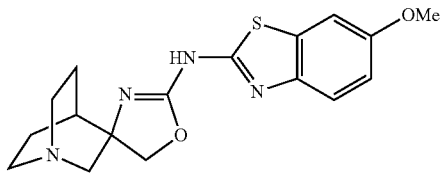 [SMILES: COc1ccc2nc(NC3=NC4(CO3)CN3CCC4CC3)sc2c1]

(3-Aminoquinuclidin-3-yl)methanol (100 mg, 0.640 mmol) was added to a stirred solution of N-(6-methoxybenzo[d]thiazol-2-yl)-1H-imidazole-1-carbothioamide (223 mg, 0.768 mmol) in DMF (2.1 mL) at 85° C. in a preheated oil bath. The reaction mixture was stirred for 3 h at that temperature before the reaction was complete by LC/MS. DIC (299 μL, 1.92 mmol) was added to the reaction mixture via syringe at 85° C., and the reaction was stirred at that temperature. After 16 h, the reaction vessel was removed from the oil bath and allowed to cool to ambient temperature. The volatiles were removed in vacuo and the residue was purified by silica gel chromatography (0-10% 9:1 methanol:ammonium hydroxide-chloroform) to afford N-(6-methoxybenzo[d]thiazol-2-yl)-5H-1'-azaspiro[oxazole-4,3'-bicyclo[2.2.2]octan]-2-amine (15 mg, 0.029 mmol, 5% yield) as a white solid. $^1$H NMR (400 MHz, DMSO-$d_6$) δ 9.70 (s, 1H), 7.57 (d, J=9.3 Hz, 1H), 7.49 (d, J=2.0 Hz, 1H), 7.07-6.98 (m, 1H), 3.81 (s, 3H), 3.73-3.42 (m, 2H), 3.41-3.13 (m, 4H), 2.31-2.04 (m, 1H), 2.01-1.81 (m, 3H). MS (LC/MS) R.T.=0.60, [M+H]$^+$=345.09.

EXAMPLE 68

N-(5-Phenylthiazol-2-yl)-5H-1'-azaspiro[oxazole-4,3'-bicyclo[2.2.2]octan]-2-amine

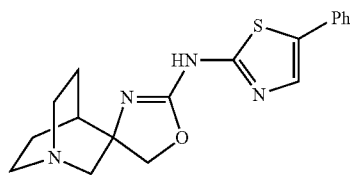 [SMILES: c1ccc(-c2cnc(NC3=NC4(CO3)CN3CCC4CC3)s2)cc1]

N-(5-Phenylthiazol-2-yl)-5H-1'-azaspiro[oxazole-4,3'-bicyclo[2.2.2]octan]-2-amine (9 mg, 0.020 mmol, 6% yield) was synthesized according to example 68. Final purification was completed by HPLC in TFA/methanol/water, affording the final product as the TFA salt. $^1$H NMR (400 MHz, CHLOROFORM-d) δ 7.71 (s, 2H), 7.55-7.45 (m, 3H), 7.32-7.28 (m, 2H), 7.03-7.00 (m, 1H), 4.81 (d, J=9.0 Hz, 1H), 4.61 (d, J=9.0 Hz, 1H), 3.70-3.53 (m, 3H), 3.52-3.38 (m, 2H), 3.36-3.24 (m, 1H), 2.90-2.82 (m, 1H), 2.04-1.89 (m, 4H). MS (LC/MS) R.T.=0.72, [M+H]$^+$=341.11.

EXAMPLE 69

N-(7-Chloropyrrolo[1,2-f][1,2,4]triazin-4-yl)-5H-1'-azaspiro[oxazole-4,3'-bicyclo[2.2.2]octan]-2-amine

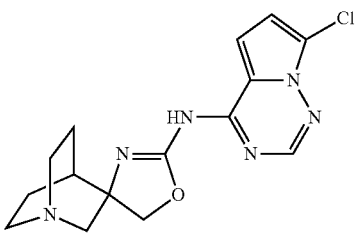 [SMILES: Clc1ccc2c(NC3=NC4(CO3)CN3CCC4CC3)ncnn12]

N-(7-Chloropyrrolo[1,2-f][1,2,4]triazin-4-yl)-5H-1'-azaspiro[oxazole-4,3'-bicyclo[2.2.2]octan]-2-amine (3.4 mg, 0.0094 mmol, 4% yield) was synthesized from (3-Aminoquinuclidin-3-yl)methanol according to example 64. $^1$H NMR (500 MHz, METHANOL-$d_4$) δ 8.23 (s, 1H), 7.05 (d, J=4.7 Hz, 1H), 6.75 (d, J=4.6 Hz, 1H), 4.80 (d, J=9.1 Hz, 1H), 4.41 (d, J=9.1 Hz, 1H), 3.29-3.14 (m, 2H), 3.12-2.77 (m, 4H), 2.08 (t, J=3.1 Hz, 1H), 2.04-1.96 (m, 1H), 1.90-1.72 (m, 3H). MS (LC/MS) R.T.=1.20, [M+H]$^+$=333.13.

EXAMPLE 70

N-(6-Methoxybenzo[d]thiazol-2-yl)-4,5-dihydro-1'-azaspiro[[1,3]oxazine-6,3'-bicyclo[2.2.2]octan]-2-amine

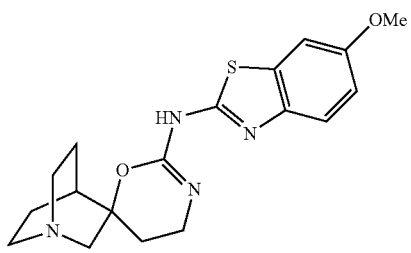 [SMILES: COc1ccc2nc(NC3=NCCC4(CN5CCC4CC5)O3)sc2c1]

N-(6-Methoxybenzo[d]thiazol-2-yl)-4,5-dihydro-1'-azaspiro[[1,3]oxazine-6,3'-bicyclo[2.2.2]octan]-2-amine, trifluoroacetic acid salt (150 mg, 0.881 mmol, 36% yield) was synthesized from 3-(2-aminoethyl)quinuclidin-3-ol according to example 1. $^1$H NMR (400 MHz, DMSO-$d_6$) δ 10.45-9.95 (m, 2H), 7.62-7.43 (m, 2H), 7.09 (d, J=7.5 Hz, 1H), 3.82 (s, 3H), 3.73-3.40 (m, 6H), 3.38-3.20 (m, 2H), 2.41-2.23 (m, 3H), 2.06-1.83 (m, 3H). MS (LC/MS) R.T.=1.00, [M+H]$^+$=358.95.

The compounds in Table 10 were synthesized according to the method of Example 70 using the appropriate commercially available amine.

TABLE 10

| Example Number | R₁ | LCMS Ion (min) | [M + H]⁺ | ¹H NMR |
|---|---|---|---|---|
| 71 | thiazole-Ph | 1.08 | 354.96 | ¹H NMR (400 MHz, DMSO-d₆) δ 10.68 (br.s., 1H), 9.78 (br. s, 1H), 7.86 (d, J = 7.3 Hz, 2H), 7.56 (s, 1H), 7.54-7.40 (m, 3H), 3.75-3.68 (m, 1H), 3.66-3.39 (m, 5H), 3.38-3.20 (m, 2H), 2.43-2.22 (m, 3H), 2.05-1.86 (m, 3H) |
| 74 | benzothiazole | 0.71 | 329.11 | ¹H NMR (400 MHz, DMSO-d₆) δ 10.49-10.06 (m, 2H), 7.90 (d, J = 8.0 Hz, 1H), 7.59 (d, J = 7.5 Hz, 1H), 7.48 (t, J = 7.8 Hz, 1H), 7.40-7.30 (m, 1H), 3.77-3.20 (m, 8H), 2.43-2.23 (m, 3H), 2.08-1.78 (m, 3H) |
| 77 | benzimidazole | 0.72 | 312.24 | ¹H NMR (400 MHz, DMSO-d₆) δ 10.59 (br. s., 1H), 9.28 (br. s., 1H), 8.57-8.30 (m, 2H), 7.31 (d, J = 12.5 Hz, 1H), 7.24-7.14 (m, 1H), 7.12-6.99 (m, 1H), 4.01-3.88 (m, 1H), 3.84-3.75 (m, 1H), 3.74-3.63 (m, 1H), 3.58-3.44 (m, 2H), 3.40-3.27 (m, 4H), 2.39-2.30 (m, 1H), 2.26-2.12 (m, 1H), 2.03 (s, 1H), 1.98-1.77 (m, 3H) |

EXAMPLE 72

N-(5-Chloropyrazin-2-yl)-4,5-dihydro-1'-azaspiro[[1,3]oxazine-6,3'-bicyclo[2.2.2]octan]-2-amine

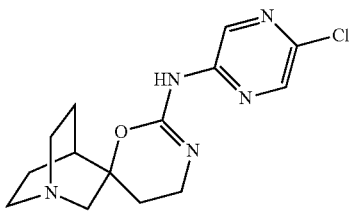

N-(5-Chloropyrazin-2-yl)-4,5-dihydro-1'-azaspiro[[1,3]oxazine-6,3'-bicyclo[2.2.2]octan]-2-amine (59 mg, 0.17 mmol, 19% yield) was synthesized from 3-(2-aminoethyl)quinuclidin-3-ol according to example 7. $^1$H NMR (400 MHz, DMSO-$d_6$) δ 10.36 (br. s., 1H), 8.52 (d, J=1.0 Hz, 1H), 8.41 (s, 1H), 3.78-3.63 (m, 2H), 3.63-3.50 (m, 2H), 3.49-3.37 (m, 1H), 3.25 (d, J=8.0 Hz, 3H), 2.50-2.38 (m, 2H), 2.37-2.14 (m, 2H), 2.07-1.81 (m, 3H). MS (LC/MS) R.T.=0.13, [M+H]$^+$=308.06.

The compounds in Table 11 were synthesized according to the method of Example 72 using the appropriate commercially available amine.

TABLE 11

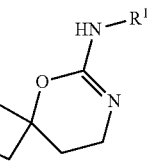

| Example Number | R₁ | LCMS RT (min) | LCMS Ion [M + H]⁺ | ¹H NMR |
|---|---|---|---|---|
| 73[a] | thiazol-2-yl | 0.12 | 279.09 | ¹HNMR (400 MHz, DMSO-d₆) δ 10.64 (br. s., 1H), 9.87 (br. s., 1H), 7.56 (d, J = 4.5 Hz, 1H), 7.25 (d, J = 4.5 Hz, 1H), 3.76-3.65 (m, 1H), 3.64-3.38 (m, 5H), 3.36-3.20 (m, 2H), 2.39-2.19 (m, 3H), 2.05-1.85 (m, 3H) |
| 75[b] | 5-chloropyridin-2-yl | 0.31 | 307.10 | ¹H NMR (400 MHz, METHANOL-d₄) δ 8.42 (d, J = 2.0 Hz, 1H), 7.98 (dd, J = 8.8, 2.5 Hz, 1H), 7.16 (d, J = 8.8 Hz, 1H), 3.89-3.63 (m, 4H), 3.60-3.51 (m, 1H), 3.50-3.35 (m, 3H), 2.68-2.60 (m, 1H), 2.59-2.32 (m, 3H), 2.25-2.00 (m, 3H) |
| 76[b] | isoquinolin-3-yl | 0.67 | 323.11 | ¹H NMR (400 MHz, DMSO-d₆) δ 12.14 (br. s., 1H), 11.44 (br. s., 1H), 10.44 (br. s., 1H), 9.28 (s, 1H), 8.26 (d, J = 8.3 Hz, 1H), 8.05 (d, J = 8.3 Hz, 1H), 7.85 (ddd, J = 8.2, 7.0, 1.1 Hz, 1H), 7.68 (td, J = 7.5, 1.0 Hz, 1H), 7.61 (s, 1H), 3.87-3.71 (m, 2H), 3.69-3.59 (m, 2H), 3.55-3.42 (m, 1H), 3.39-3.15 (m, 3H), 2.51-2.44 (m, 2H), 2.40-2.18 (m, 2H), 2.08-1.81 (m, 3H) |
| 76a[c] | isoquinolin-3-yl | 0.62 | 323.28 | ¹H NMR (500 MHz, METHANOL-d₄) δ 9.00 (s, 1H), 7.94 (d, J = 8.5 Hz, 1H), 7.72 (d, J = 7.6 Hz, 1H), 7.60 (ddd, J = 8.2, 6.9, 1.1 Hz, 1H), 7.45-7.39 (m, 1H), 7.32 (br. s., 1H), 3.63-3.51 (m, 2H), 3.09-2.76 (m, 6H), 2.29-2.10 (m, 4H), 1.85-1.65 (m, 2H), 1.61-1.51 (m, 1H) |
| 76b[c] | isoquinolin-3-yl | 0.62 | 323.28 | ¹H NMR (500 MHz, METHANOL-d₄) δ 9.00 (s, 1H), 7.94 (d, J = 8.5 Hz, 1H), 7.72 (d, J = 7.6 Hz, 1H), 7.60 (ddd, J = 8.2, 6.9, 1.1 Hz, 1H), 7.45-7.39 (m, 1H), 7.32 (br. s., 1H), 3.63-3.51 (m, 2H), 3.09-2.76 (m, 6H), 2.29-2.10 (m, 4H), 1.85-1.65 (m, 2H), 1.61-1.51 (m, 1H) |

TABLE 11-continued
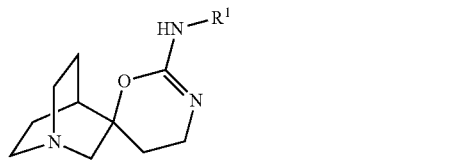
| Example Number | R₁ | LCMS RT (min) | LCMS Ion [M + H]⁺ | ¹H NMR |
|---|---|---|---|---|
| 78ᵃ | ![pyrimidine-Cl] 2-(5-chloropyrimidinyl) | 0.21 | 308.12 | ¹H NMR (400 MHz, DMSO-d₆) δ 11.34-10.38 (m, 2H), 8.92 (s, 2H), 3.82-3.70 (m, 2H), 3.64-3.53 (m, 2H), 3.45 (s, 1H), 3.35-3.21 (m, 3H), 2.50-2.43 (m, 1H), 2.39-2.20 (m, 2H), 2.09-1.73 (m, 3H) |
| 81ᵃ | ![5,6-dimethyl-1,2,4-triazin-3-yl] | 0.17 | 303.30 | ¹H NMR (400 MHz, DMSO-d₆) δ 10.92 (br. s., 1H), 10.37 (br. s., 1H), 3.82-3.53 (m, 4H), 3.45 (s, 1H), 3.34-3.19 (m, 3H), 2.63 (s, 3H), 2.60 (s, 3H), 2.47-2.41 (m, 1H), 2.36-2.23 (m, 2H), 2.06-1.80 (m, 3H) |
| 83ᵃ | ![6-chloropyridazin-3-yl] | 0.19 | 308.19 | ¹H NMR (500 MHz, METHANOL-d₄) δ 7.95-7.90 (m, 1H), 7.59-7.53 (m, 1H), 3.94-3.85 (m, 2H), 3.83-3.75 (m, 1H), 3.74-3.67 (m, 1H), 3.61-3.52 (m, 1H), 3.51-3.35 (m, 3H), 2.70-2.64 (m, 1H), 2.63-2.55 (m, 1H), 2.55-2.47 (m, 1H), 2.46-2.36 (m, 1H), 2.24-2.02 (m, 3H) |
| 84 | ![quinazolin-2-yl] | 0.45 | 324.25 | ¹H NMR (400 MHz, METHANOL-d₄) δ 9.26 (d, J = 0.8 Hz, 1H), 7.92-7.87 (m, 1H), 7.87-7.74 (m, 2H), 7.46 (ddd, J = 8.0, 6.7, 1.4 Hz, 1H), 3.72-3.64 (m, 2H), 3.15-2.74 (m, 6H), 2.29-2.16 (m, 4H), 1.88-1.69 (m, 2H), 1.65-1.49 (m, 1H) |

TABLE 11-continued

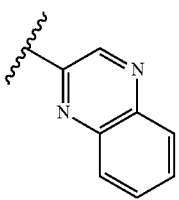 [SMILES: *c1cnc2ccccc2n1]

| Example Number | R₁ | LCMS RT (min) | LCMS Ion [M + H]⁺ | ¹H NMR |
|---|---|---|---|---|
| 85[d] | 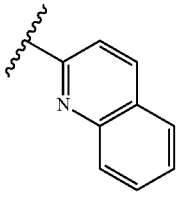 [SMILES: *c1ccc2ccccc2n1] | 0.48 | 324.25 | ¹H NMR (400 MHz, METHANOL-d₄) δ 8.76 (s, 1H), 8.20 (dd, J = 8.3, 1.0 Hz, 1H), 8.11 (dd, J = 8.4, 1.4 Hz, 1H), 7.88 (ddd, J = 8.3, 7.0, 1.5 Hz, 1H), 7.84-7.78 (m, 1H), 4.03-3.83 (m, 3H), 3.72 (dd, J = 14.6, 2.3 Hz, 1H), 3.63-3.53 (m, 1H), 3.53-3.38 (m, 3H), 2.74-2.39 (m, 4H), 2.26-2.03 (m, 3H) |
| 86[b] | | 0.61 | 323.23 | ¹H NMR (400 MHz, DMSO-d₆) δ 12.51 (br. s., 1H), 12.07 (br. g., 1H), 10.56 (br. s., 1H), 8.52 (d, J = 8.8 Hz, 1H), 8.31 (br. s, 1H), 8.01 (d, J = 7.5 Hz, 1H), 7.85 (ddd, J = 8.4, 7.0, 1.4 Hz, 1H), 7.65-7.59 (m, 1H), 7.40 (d, J = 7.5 Hz, 1H), 3.96-3.78 (m, 2H), 3.76-3.59 (m, 2H), 3.53-3.40 (m, 1H), 3.38-3.21 (m, 3H), 2.57-2.54 (m, 1H), 2.43-2.19 (m, 2H), 2.09-1.83 (m, 3H) |

[a]Isolated as the trifluoroacetic acid salt.
[b]Isolated as the bis trifluoroacetic acid salt.
[c]The enantiomers were separated using a Chiralpak OJ-H (4.6 × 250 mm, 5 μm) column with a mobile phase consisting of 15% methanol (0.1% DEA) in CO₂. The wavelength was set at 320 nM. The separated peaks were concentrated in vacuo to yield colorless oils as the free base.
[b]Purified by silica gel column chromatography using ammonium hydroxide/methanol/chloroform.

EXAMPLE 79

N-(5-Methoxythiazolo[5,4-d]pyrimidin-2-yl)-4,5-dihydro-1'-azaspiro[[1,3]oxazine-6,3'-bicyclo[2.2.2]octan]-2-amine

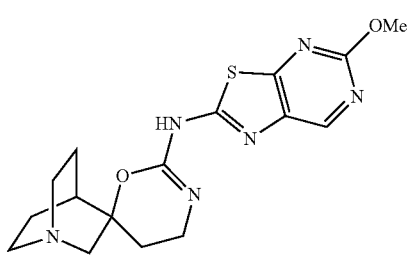 [SMILES: COc1ncc2nc(NC3=NCCC4(CN5CCC4CC5)O3)sc2n1]

N-(5-Methoxythiazolo[5,4-d]pyrimidin-2-yl)-4,5-dihydro-1'-azaspiro[[1,3]oxazine-6,3'-bicyclo[2.2.2]octan]-2-amine, trifluoroacetic acid salt (8.1 mg, 0.017 mmol, 3% yield) was synthesized from 3-(2-aminoethyl)quinuclidin-3-ol according to example 19, step C, and purified using reverse phase chromatography eluting with a water/TFA/methanol mixture. ¹H NMR (400 MHz, METHANOL-d₄) δ 8.68 (s, 1H), 4.05 (s, 3H), 3.82-3.57 (m, 4H), 3.55-3.35 (m, 4H), 2.65-2.55 (m, 1H), 2.49-2.36 (m, 3H), 2.22-1.97 (m, 3H). MS (LC/MS) R.T.=0.88, [M+H]⁺=360.90.

The compounds in Table 12 were synthesized according to the method of Example 79 using the appropriate commercially available amine.

TABLE 12

| Example Number | R₁ | LCMS RT (min) | LCMS Ion [M + H]⁺ | ¹H NMR |
|---|---|---|---|---|
| 80 | pyrimidine-OMe | 0.39 | 303.90 | ¹H NMR (400 MHz, METHANOL-d₄) δ 8.65 (s, 1 H), 6.48 (s, 1 H), 4.03 (s, 3 H), 3.91-3.80 (m, 2 H), 3.70-3.64 (m, 1 H), 3.79-3.63 (m, 1 H), 3.60-3.49 (m, 1 H), 3.49-3.34 (m, 3 H), 2.69-2.61 (m, 1 H), 2.60-2.32 (m, 3 H), 2.23-1.97 (m, 3 H) |
| 82 | quinazoline | 0.51 | 324.25 | ¹H NMR (500 MHz, METHANOL-d4) δ 8.79 (s, 1 H), 8.52 (d, J = 8.2 Hz, 1 H), 8.06-8.01 (m, 1 H), 7.81-7.72 (m, 2 H), 3.89-3.69 (m, 3 H), 3.69-3.63 (m, 1 H), 3.56-3.48 (m, 1 H), 3.47-3.37 (m, 3 H), 2.67-2.60 (m, 1 H), 2.58-2.27 (m, 3 H), 2.22-1.97 (m, 3 H) |
| 87a | thiazolo-pyridine-Br | 1.12 | 409.2 | ¹H NMR (500 MHz, DMSO-d₆) δ 10.56 (br. s., 1 H), 7.89 (d, J = 7.0 Hz, 1 H), 7.60 (d, J = 6.1 Hz, 1 H), 3.59-3.41 (m, 2 H), 2.79-2.55 (m, 6 H), 2.00-1.82 (m, 3 H), 1.74-1.68 (m, 1 H), 1.67-1.56 (m, 1 H), 1.50-1.39 (m, 1 H), 1.29-1.17 (m, 1 H) |
| 88[a,b] | pyrrolotriazine-Cl | 1.12 | 347.16 | ¹H NMR (400 MHz, METHANOL-d4) δ 8.08 (s, 1 H), 7.06 (d, J = 4.8 Hz, 1 H), 6.68 (d, J = 4.8 Hz, 1 H), 3.65 (s, 2 H), 3.16-2.73 (m, 6 H), 2.30-2.16 (m, 4 H), 1.87-1.69 (m, 2 H), 1.65-1.51 (m, 1 H) |

[a] Isolated as the free base.
[b] The reaction was stirred at 60° C. for 45 min.

EXAMPLE 89

(Z)-6-Methoxy-N-(3-methyl-1'-azaspiro[oxazolidine-5,3'-bicyclo[2.2.2]octane]-2-ylidene)benzo[d]thiazol-2-amine

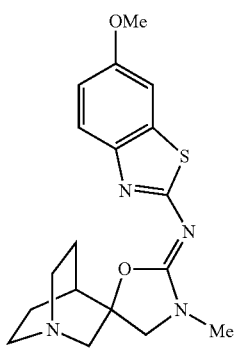 [SMILES: COc1ccc2nc(/N=C3\OC4(CN5CCC4CC5)CN3C)sc2c1]

3-((Methylamino)methyl)quinuclidin-3-ol (154 mg, 0.905 mmol) was added to a stirred solution of N-(6-methoxybenzo[d]thiazol-2-yl)-1H-imidazole-1-carbothioamide (249 mg, 0.905 mmol, prepared in Example 1, step A) in DMF (3.0 mL) at 70° C. in a preheated oil bath. The reaction mixture was stirred for 16 h at that temperature before the reaction was complete by LC/MS. DIC (423 µL, 2.71 mmol) was added to the reaction mixture via syringe at 70° C., and the reaction was stirred at that temperature. After 16 h, the reaction vessel was removed from the oil bath and allowed to cool to ambient temperature. The volatiles were removed in vacuo and the residue was purified by silica gel chromatography (0-30% 9:1 methanol:ammonium hydroxide-chloroform) followed by purification by reverse phase preparatory HPLC (0-100% TFA-methanol-water) to afford (E)-6-methoxy-N-(3-methyl-1'-azaspiro[oxazolidine-5,3'-bicyclo[2.2.2]octane]-2-ylidene)benzo[d]thiazol-2-amine as the trifluoroacetic acid salt (206 mg, 0.436 mmol, 48% yield) as a white solid. $^1$H NMR (400 MHz, DMSO-d$_6$) δ 10.21 (br. s., 1H), 7.57-7.45 (m, 2H), 7.05 (d, J=9.0 Hz, 1H), 4.07 (d, J=10.0 Hz, 1H), 3.90-3.67 (m, 7H), 3.61-3.46 (m, 1H), 3.43-3.17 (m, 3H), 3.04 (s, 3H), 2.29 (t, J=10.5 Hz, 1H), 2.12-1.73 (m, 3H). MS (LC/MS) R.T.=0.73, [M+H]$^+$= 359.10.

EXAMPLE 90

(Z)—N-(3-Methyl-1'-azaspiro[oxazolidine-5,3'-bicyclo[2.2.2]octane]-2-ylidene)-5-phenylthiazol-2-amine

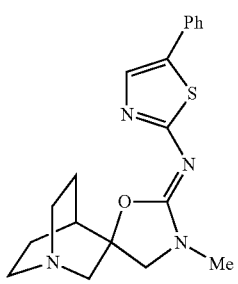 [SMILES: CN1CC2(CN3CCC2CC3)O/C1=N\c1ncc(-c2ccccc2)s1]

(Z)—N-(3-Methyl-1'-azaspiro[oxazolidine-5,3'-bicyclo[2.2.2]octane]-2-ylidene)-5-phenylthiazol-2-amine, trifluoroacetic acid salt (125 mg, 0.266 mmol, 29% yield) was synthesized from 3-((methylamino)methyl)quinuclidin-3-ol according to example 89. $^1$H NMR (400 MHz, DMSO-d$_6$) δ 10.12 (br. s., 1H), 7.92-7.83 (m, 2H), 7.60 (s, 1H), 7.50-7.42 (m, 2H), 7.40-7.31 (m, 1H), 4.06-3.95 (m, 1H), 3.85-3.75 (m, 2H), 3.75-3.66 (m, 1H), 3.57-3.42 (m, 1H), 3.37-3.21 (m, 3H), 3.03 (s, 3H), 2.47-2.47 (m, 1H), 2.51-2.46 (m, 1H), 2.31-2.18 (m, 1H), 2.08-1.79 (m, 3H). (LC/MS) R.T.=0.73, [M+H]$^+$=355.11.

EXAMPLE 91

(Z)-5-Chloro-N-(3-methyl-1'-azaspiro[oxazolidine-5,3'-bicyclo[2.2.2]octane]-2-ylidene)pyrazin-2-amine

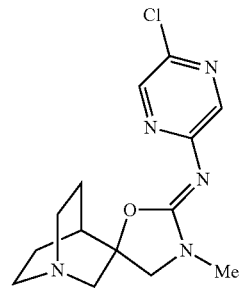 [SMILES: CN1CC2(CN3CCC2CC3)O/C1=N\c1cnc(Cl)cn1]

To 3-((methylamino)methyl)quinuclidin-3-ol (0.150 g, 0.881 mmol) in N,N-dimethylformamide (2.9 mL) was added dimethyl 5-chloropyrazin-2-ylcarbonimidodithioate (206 mg, 0.881 mmol). The suspension stirred at ambient temperature for 4 h. No product was observed by LC/MS. The reaction vessel was subsequently placed into a preheated oil-bath and stirred at 50° C. for 16 h. The reaction flask was removed from the oil-bath and allowed to cool to ambient temperature. The mixture was concentrated and purified by silica gel chromatography (0-30% 9:1 methanol:ammonium hydroxide-chloroform), followed by reverse phase preparatory HPLC (water-TFA-methanol). The product fractions were combined and concentrated in vacuo to afford (Z)-5-chloro-N-(3-methyl-1'-azaspiro[oxazolidine-5,3'-bicyclo[2.2.2]octane]-2-ylidene)pyrazin-2-amine, trifluoroacetic acid salt (4.1 mg, 0.0097 mmol, 1% yield) as a colorless oil. $^1$H NMR (400 MHz, METHANOL-d$_4$) δ 8.29 (d, J=1.5 Hz, 1H), 8.15 (d, J=1.5 Hz, 1H), 3.94 (d, J=9.8 Hz, 1H), 3.82-3.75 (m, 1H), 3.71-3.61 (m, 2H), 3.52-3.38 (m, 3H), 3.28-3.21 (m, 1H), 3.05 (s, 3H), 2.53-2.48 (m, 1H), 2.33-2.20 (m, 1H), 2.11 (m, 1H), 2.05-1.90 (m, 2H). MS (LC/MS) R.T.=0.34; [M+H]$^1$=308.06.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of formula I, or a stereoisomer thereof,

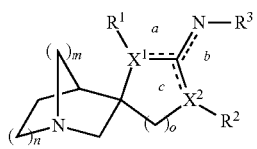

wherein
$X^1$ is nitrogen; $X^2$ is nitrogen; m is 1 or 2; n is 1 or 2; o is 1 or 2; a is a single bond; b is a single bond; c is a double bond; $R^1$ is selected from the group consisting of hydrogen, methyl, and ethyl; and $R^2$ is absent;
$R^3$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinazolinyl, quinoxalinyl, naphthyridinyl, indazolyl, indolyl, 2-indolonyl, benzisoxazolyl, benzoisothiazolyl, benzoxazolyl, benzothiazolyl, benzimidazolyl, furopyridinyl, oxazolopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, imidazopyridinyl, pyrrolopyrimidinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, and tetrahydrobenzothiazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^4R^5$, pyrrolidinonyl, methylenedioxy, furyl, thienyl, pyrazolyl, imidazolyl, thiazolyl, triazolyl, pyrazinyl, pyrimidinyl, naphthyl, $C_{1-4}$alkylamido, $CONR^4R^5$, pyridyl, phenyl, and benzyl, and where imidazolyl, pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^4R^5$;
$R^4$ is hydrogen, $C_{1-4}$alkyl, $C_{1-4}$hydroxyalkyl, or $C_{1-4}$aminoalkyl; and
$R^5$ is hydrogen, $C_{1-4}$alkyl, $C_{1-4}$hydroxyalkyl, or $C_{1-4}$aminoalkyl;
or $R^4$ and $R^5$ taken together with the nitrogen atom to which they are attached is azetidinyl, pyrrolidinyl, piperidinyl, piperazinyl, N—($C_{1-4}$alkyl)piperazinyl, morpholinyl, or homopiperidinyl;
or a pharmaceutically acceptable salt thereof.
2. A compound of claim 1 where
$X^1$ is nitrogen; $X^2$ is nitrogen; m is 2; n is 1; o is 1; a is a single bond; b is a single bond; c is a double bond; $R^1$ is selected from the group consisting of hydrogen, methyl, and ethyl; and $R^2$ is absent;
$R^3$ is selected from the group consisting of thiazolyl, pyridinyl, pyrazinyl, pyridazinyl, pyrimidinyl, triazinyl, quinolinyl, isoquinolinyl, quinazolinyl, quinoxalinyl, indazolyl, benzoxazolyl, benzothiazolyl, benzimidazolyl, oxazolopyridinyl, thiazolopyridinyl, thiazolopyridinonyl, thiazolopyrazinyl, thiazolopyrimidinyl, triazolopyridinyl, imidazopyridinyl, and pyrrolotriazinyl, and is substituted with 0-3 substituents independently selected from the group consisting of $C_{1-4}$alkyl, $C_{1-4}$haloalkyl, $C_{1-4}$alkoxy, benzyloxy, halo, $NR^4R^5$, imidazolyl, and phenyl;
$R^4$ is $C_{1-4}$alkyl; and
$R^5$ is $C_{1-4}$alkyl; and
or a pharmaceutically acceptable salt thereof.
3. A compound of claim 1 where $X^1$ is nitrogen; $X^2$ is nitrogen; m is 2; n is 1; o is 1; a is a single bond; b is a single bond; c is a double bond; $R^1$ is selected from the group consisting of hydrogen, methyl, and ethyl; $R^2$ is absent; or a pharmaceutically acceptable salt thereof.
4. A compound of claim 1 where
$R^3$ is selected from the group consisting of thiazolyl, pyridinyl, pyrazinyl, pyridazinyl, pyrimidinyl, triazinyl, quinolinyl, isoquinolinyl, quinazolinyl, quinoxalinyl, indazolyl, benzoxazolyl, benzothiazolyl, benzimidazolyl, oxazolopyridinyl, thiazolopyridinyl, thiazolopyridinonyl, thiazolopyrazinyl, thiazolopyrimidinyl, triazolopyridinyl, imidazopyridinyl, and pyrrolotriazinyl, and is substituted with 0-3 substituents independently selected from the group consisting of $C_{1-4}$alkyl, $C_{1-4}$haloalkyl, $C_{1-4}$alkoxy, benzyloxy, halo, $NR^4R^5$, imidazolyl, and phenyl;
$R^4$ is $C_{1-4}$ alkyl; and
$R^5$ is $C_{1-4}$alkyl;
or a pharmaceutically acceptable salt thereof.
5. The stereoisomer of claim 1 according to Formula Ia;

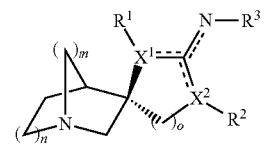

or a pharmaceutically acceptable salt thereof.
6. A compound of claim 1 selected from the group consisting of
N-(6-methoxy-1,3-benzothiazol-2-yl)-1',5'-dihydrospiro[4-azabicyclo[2.2.2]octane-2,4'-imidazol]-2'-amine;
N-(6-methoxy-1,3-benzothiazol-2-yl)-3'-methyl-3',5'-dihydrospiro[4-azabicyclo[2.2.2]octane-2,4'-imidazol]-2'-amine;
3'-ethyl-N-(6-methoxy-1,3-benzothiazol-2-yl)-3',5'-dihydrospiro[4-azabicyclo[2.2.2]octane-2,4'-imidazol]-2'-amine;
N-(5-phenyl-1,3-thiazol-2-yl)-1',5'-dihydrospiro[4-azabicyclo[2.2.2]octane-2,4'-imidazol]-2'-amine;
3'-methyl-N-(5-phenyl-1,3-thiazol-2-yl)-3',5'-dihydrospiro[4-azabicyclo[2.2.2]octane-2,4'-imidazol]-2'-amine;
3'-ethyl-N-(5-phenyl-1,3-thiazol-2-yl)-3',5'-dihydrospiro[4-azabicyclo[2.2.2]octane-2,4'-imidazol]-2'-amine;
N-(5-chloro-2-pyrazinyl)-1',5'-dihydrospiro[4-azabicyclo[2.2.2]octane-2,4'-imidazol]-2'-amine;
N-(6-methyl-1,3-benzoxazol-2-yl)-1',5'-dihydrospiro[4-azabicyclo[2.2.2]octane-2,4'-imidazol]-2'-amine;
N-(6-methyl-1,3-benzoxazol-2-yl)-1',5'-dihydrospiro[4-azabicyclo[2.2.2]octane-2,4'-imidazol]-2'-amine;
N-(6-methyl-1,3-benzoxazol-2-yl)-1',5'-dihydrospiro[4-azabicyclo[2.2.2]octane-2,4'-imidazol]-2'-amine;
N-1,3-thiazol-2-yl-1',5'-dihydrospiro[4-azabicyclo[2.2.2]octane-2,4'-imidazol]-2'-amine;

3'-methyl-N-1,3-thiazol-2-yl-3',5'-dihydrospiro[4-azabi-cyclo[2.2.2]octane-2,4'-imidazol]-2'-amine;
N-1,3-benzothiazol-2-yl-1',5'-dihydrospiro[4-azabicyclo[2.2.2]octane-2,4'-imidazol]-2'-amine;
N-1,3-benzothiazol-2-yl-1',5'-dihydrospiro[4-azabicyclo[2.2.2]octane-2,4'-imidazol]-2'-amine;
N-1,3-benzothiazol-2-yl-1',5'-dihydrospiro[4-azabicyclo[2.2.2]octane-2,4'-imidazol]-2'-amine;
N-1,3-benzothiazol-2-yl-3'-methyl-3',5'-dihydrospiro[4-azabicyclo[2.2.2]octane-2,4'-imidazol]-2'-amine;
N-(5-chloro-2-pyridinyl)-1',5'-dihydrospiro[4-azabicyclo[2.2.2]octane-2,4'-imidazol]-2'-amine;
N-(5-chloro-2-pyridinyl)-3'-methyl-3',5'-dihydrospiro[4-azabicyclo[2.2.2]octane-2,4'-imidazol]-2'-amine;
N-3-isoquinolinyl-3'-methyl-3',5'-dihydrospiro[4-azabi-cyclo[2.2.2]octane-2,4'-imidazol]-2'-amine;
N-1H-benzimidazol-2-yl-1',5'-dihydrospiro[4-azabicyclo[2.2.2]octane-2,4'-imidazol]-2'-amine;
N-(5-chloro-2-pyrimidinyl)-1',5'-dihydrospiro[4-azabicy-clo[2.2.2]octane-2,4'-imidazol]-2'-amine;
N-(5-chloro-2-pyrimidinyl)-3'-methyl-3',5'-dihydrospiro[4-azabicyclo[2.2.2]octane-2,4'-imidazol]-2'-amine;
N-(5-methoxy[1,3]thiazolo[5,4-d]pyrimidin-2-yl)-1',5'-dihydrospiro[4-azabicyclo[2.2.2]octane-2,4'-imida-zol]-2'-amine;
N-(6-methoxy-4-pyrimidinyl)-1',5'-dihydrospiro[4-azabi-cyclo[2.2.2]octane-2,4'-imidazol]-2'-amine;
N-(6-methoxy-4-pyrimidinyl)-3'-methyl-3',5'-dihy-drospiro[4-azabicyclo[2.2.2]octane-2,4'-imidazol]-2'-amine;
N-(5,6-dimethyl-1,2,4-triazin-3-yl)-3'-methyl-3',5'-dihy-drospiro[4-azabicyclo[2.12]octane-2,4'-imidazol]-2'-amine;
N-4-quinazolinyl-1',5'-dihydrospiro[4-azabicyclo[2.2.2]octane-2,4'-imidazol]-2'-amine;
3'-methyl-N-4-quinazolinyl-3',5'-dihydrospiro[4-azabicy-clo[2.2.2]octane-2,4'-imidazol]-2'-amine;
N-(6-chloro-3-pyridazinyl)-1',5'-dihydrospiro[4-azabicy-clo[2.2.2]octane-2,4'-imidazol]-2'-amine;
N-(6-chloro-3-pyridazinyl)-3'-methyl-3',5'-dihydrospiro[4-azabicyclo[2.2.2]octane-2,4'-imidazol]-2'-amine;
3'-methyl-N-2-quinazolinyl-3',5'-dihydrospiro[4-azabicy-clo[2.2.2]octane-2,4'-imidazol]-2'-amine;
N-(5-chloro[1,3]thiazolo[5,4-b]pyridin-2-yl)-1',5'-dihy-drospiro[4-azabicyclo[2.2.2]octane-2,4'-imidazol]-2'-amine;
N-(5-chloro[1,3]thiazolo[5,4-b]pyridin-2-yl)-1',5'-dihy-drospiro[4-azabicyclo[2.2.2]octane-2,4'-imidazol]-2'-amine;
N-(5-chloro[1,3]thiazolo[5,4-b]pyridin-2-yl)-1',5'-dihy-drospiro[4-azabicyclo[2.2.2]octane-2,4'-imidazol]-2'-amine;
N-(5-chloro[1,3]thiazolo[5,4-b]pyridin-2-yl)-3'-methyl-3',5'-dihydrospiro[4-azabicyclo[2.2.2]octane-2,4'-imi-dazol]-2'-amine
N-(6-bromo[1,3]thiazolo[4,5-b]pyrazin-2-yl)-1',5'-dihy-drospiro[4-azabicyclo[2.2.2]octane-2,4'-imidazol]-2'-amine;
N-(6-bromo[1,3]thiazolo[4,5-b]pyrazin-2-yl)-3'-methyl-3',5'-dihydrospiro[4-azabicyclo[2.2.2]octane-2,4'-imi-dazol]-2'-amine;
N-[1,3]thiazolo[4,5-b]pyrazin-2-yl-1',5'-dihydrospiro[4-azabicyclo[2.2.2]octane-2,4'-imidazol]-2'-amine;
3'-methyl-N-[1,3]thiazolo[4,5-b]pyrazin-2-yl-3',5'-dihy-drospiro[4-azabicyclo[2.2.2]octane-2,4'-imidazol]-2'-amine;
N-[1,2,4]triazolo[1,5-a]pyridin-2-yl-1',5'-dihydrospiro[4-azabicyclo[2.2.2]octane-2,4'-imidazol]-2'-amine;
3'-methyl-N-[1,2,4]triazolo[1,5-a]pyridin-2-yl-3',5'-dihy-drospiro[4-azabicyclo[2.2.2]octane-2,4'-imidazol]-2'-amine;
N-2-quinoxalinyl-1',5'-dihydrospiro[4-azabicyclo[2.2.2]octane-2,4'-imidazol]-2'-amine;
N-imidazo[1,2-a]pyridin-2-yl-1',5'-dihydrospiro[4-azabi-cyclo[2.2.2]octane-2,4'-imidazol]-2'-amine;
N-(7-methoxy[1,3]thiazolo[5,4-d]pyrimidin-2-yl)-1',5'-dihydrospiro[4-azabicyclo[2.2.2]octane-2,4'-imida-zol]-2'-amine;
N-(5-(benzyloxy)[1,3]thiazolo[5,4-b]pyridin-2-yl)-1',5'-dihydrospiro[4-azabicyclo[2.2.2]octane-2,4'-imida-zol]-2'-amine;
3'-methyl-N-2-quinolinyl-3',5'-dihydrospiro[4-azabicyclo[2.2.2]octane-2,4'-imidazol]-2'-amine;
N-(6-methyl[1,3]thiazolo[4,5-b]pyrazin-2-yl)-1',5'-dihy-drospiro[4-azabicyclo[2.2.2]octane-2,4'-imidazol]-2'-amine;
2-(1',5'-dihydrospiro[4-azabicyclo[2.2.2]octane-2,4'-imi-dazol]-2'-ylamino)[1,3]thiazolo[5,4-b]pyridin-5(4H)-one;
N-(4,6-dimethyl-1,3,5-triazin-2-yl)-1',5'-dihydrospiro[4-azabicyclo[2.2.2]octane-2,4'-imidazol]-2'-amine;
N-(5-fluoro[1,3]thiazolo[5,4-b]pyridin-2-yl)-1',5'-dihy-drospiro[4-azabicyclo[2.2.2]octane-2,4'-imidazol]-2'-amine;
N-(5-fluoro[1,3]thiazolo[5,4-b]pyridin-2-yl)-3'-methyl-3',5'-dihydrospiro[4-azabicyclo[2.2.2]octane-2,4'-imi-dazol]-2'-amine;
N-(5-methoxy[1,3]thiazolo[5,4-b]pyridin-2-yl)-1',5'-di-hydrospiro[4-azabicyclo[2.2.2]octane-2,4'-imidazol]-2'-amine;
N-(5-methoxy[1,3]thiazolo[5,4-b]pyridin-2-yl)-3'-methyl-3',5'-dihydrospiro[4-azabicyclo[2.2.2]octane-2,4'-imidazol]-2'-amine;
N~2~-(1',5'-dihydrospiro[4-azabicyclo[2.2.2]octane-2,4'-imidazol]-2'-yl)-N~5,N~5~-dimethyl[1,3]thiazolo[5,4-b]pyridine-2,5-diamine;
N-(5-bromo[1,3]thiazolo[5,4-b]pyridin-2-yl)-1',5'-dihy-drospiro[4-azabicyclo[2.2.2]octane-2,4'-imidazol]-2'-amine;
N-(5-bromo[1,3]thiazolo[5,4-b]pyridin-2-yl)-3'-methyl-3',5'-dihydrospiro[4-azabicyclo[2.2.2]octane-2,4'-imi-dazol]-2'-amine;
(2R)—N-(6-(trifluoromethyl)-1H-indazol-3-yl)-3',5'-di-hydrospiro[4-azabicyclo[2.2.2]octane-2,4'-imidazol]-2'-amine;
N-(6-chloro-1,3-benzothiazol-2-yl)-1',5'-dihydrospiro[4-azabicyclo[2.2.2]octane-2,4'-imidazol]-2'-amine;
N-(4-chloro-1,3-benzothiazol-2-yl)-1',5'-dihydrospiro[4-azabicyclo[2.2.2]octane-2,4'-imidazol]-2'-amine;
N-(5-methoxy-1,3-benzothiazol-2-yl)-1',5'-dihydrospiro[4-azabicyclo[2.2.2]octane-2,4'-imidazol]-2'-amine;
N-(4-fluoro-1,3-benzothiazol-2-yl)-1',5'-dihydrospiro[4-azabicyclo[2.2.2]octane-2,4'-imidazol]-2'-amine;
N-[1,3]thiazolo[5,4-b]pyridin-2-yl-1',5'-dihydrospiro[4-azabicyclo[2.2.2]octane-2,4'-imidazol]-2'-amine;
N-(5-chloro-1,3-benzoxazol-2-yl)-1',5'-dihydrospiro[4-azabicyclo[2.2.2]octane-2,4'-imidazol]-2'-amine;
N-(5-chloro-1,3-benzoxazol-2-yl)-3'-methyl-3',5'-dihy-drospiro[4-azabicyclo[2.2.2]octane-2,4'-imidazol]-2'-amine;
N-1,3-benzoxazol-2-yl-1',5'-dihydrospiro[4-azabicyclo[2.2.2]octane-2,4'-imidazol]-2'-amine;

N-1,3-benzoxazol-2-yl-3'-methyl-3',5'-dihydrospiro[4-azabicyclo[2.2.2]octane-2,4'-imidazol]-2'-amine;

N-(6-(1H-imidazol-1-yl)-4-pyrimidinyl)-1',5'-dihydrospiro[4-azabicyclo[2.2.2]octane-2,4'-imidazol]-2'-amine;

N-(5-methyl[1,3]oxazolo[5,4-b]pyridin-2-yl)-1',5'-dihydrospiro[4-azabicyclo[2.2.2]octane-2,4'-imidazol]-2'-amine;

N-(6-methyl-1,3-benzothiazol-2-yl)-1',5'-dihydrospiro[4-azabicyclo[2.2.2]octane-2,4'-imidazol]-2'-amine;

N-(7-methylpyrrolo[2,1-f][1,2,4]triazin-4-yl)-1',5'-dihydrospiro[4-azabicyclo[2.2.2]octane-2,4'-imidazol]-2'-amine;

N-(7-chloropyrrolo[2,1-f][1,2,4]triazin-4-yl)-1',5'-dihydrospiro[4-azabicyclo[2.2.2]octane-2,4'-imidazol]-2'-amine; and N-(7-bromopyrrolo[2,1-f][1,2,4]triazin-4-yl)-1',5'-dihydrospiro[4-azabicyclo[2.2.2]octane-2,4'-imidazol]-2'-amine;

or a pharmaceutically acceptable salt thereof.

7. A pharmaceutical composition comprising a therapeutically effective amount of a compound of claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 9,458,179 B2
APPLICATION NO. : 14/400948
DATED : October 4, 2016
INVENTOR(S) : Hill et al.

Page 1 of 1

It is certified that error appears in the above-identified patent and that said Letters Patent is hereby corrected as shown below:

In the Claims

Claim 2, Column 86, Line 6:
After "$C_{1-4}$alkyl;" delete "and".

Claim 6, Column 87, Line 33:
Delete "[2.12]" and insert -- [2.2.2] --.

Claim 6, Column 87, Line 56:
After "amine" insert -- ; --.

Signed and Sealed this
Twenty-first Day of August, 2018

Andrei Iancu
*Director of the United States Patent and Trademark Office*